United States Patent
Chen et al.

(10) Patent No.: US 11,273,410 B2
(45) Date of Patent: Mar. 15, 2022

(54) EXTRACTED MATERIAL FOR FORWARD OSMOSIS, PREPARATION METHOD THEREOF, AND FORWARD-OSMOSIS WATER DESALINATION SYSTEM USING THE SAME

(71) Applicant: INDUSTRIAL TECHNOLOGY RESEARCH INSTITUTE, Hsinchu (TW)

(72) Inventors: Yi-Chun Chen, Hsinchu (TW); Po-I Liu, Kaohsiung (TW); Chia-Hua Ho, Miaoli (TW); Yeu-Ding Chen, Zhunan Township (TW); David Chiuni Wang, Hsinchu (TW); Ren-Yang Horng, Hsinchu (TW); Kai-Chi Chen, Tsautuen Jen (TW)

(73) Assignee: INDUSTRIAL TECHNOLOGY RESEARCH INSTITUTE, Hsinchu (TW)

( * ) Notice: Subject to any disclaimer, the term of this patent is extended or adjusted under 35 U.S.C. 154(b) by 17 days.

(21) Appl. No.: 16/731,435

(22) Filed: Dec. 31, 2019

(65) Prior Publication Data
US 2021/0197123 A1   Jul. 1, 2021

(51) Int. Cl.
*B01D 61/00* (2006.01)
*C02F 1/44* (2006.01)
(Continued)

(52) U.S. Cl.
CPC ............ *B01D 61/005* (2013.01); *C02F 1/445* (2013.01); *C07C 309/30* (2013.01); *C02F 2103/08* (2013.01)

(58) Field of Classification Search
CPC ..... B01D 61/005; C07C 309/30; C02F 1/445; C02F 2103/08
See application file for complete search history.

(56) References Cited

U.S. PATENT DOCUMENTS 9,447,239 B2   9/2016  Jung et al.
9,822,021 B2   11/2017  McGinnis et al.
(Continued)

FOREIGN PATENT DOCUMENTS

CN   108889124 A   11/2018
TW   I586681 B     6/2017
(Continued)

OTHER PUBLICATIONS

Chatel et al., "Mixing Ionic Liquids—"Simple Mixtures" or "Double Salts"?", Green Chem., vol. 16, 2014, pp. 1-63 (65 pages total).
(Continued)

*Primary Examiner* — Krishnan S Menon
(74) *Attorney, Agent, or Firm* — Birch, Stewart, Kolasch & Birch, LLP

(57) ABSTRACT

An extracted material for forward osmosis is provided. The extracted material includes a first ionic compound, a second ionic compound and a third ionic compound, which are represented by formula $\{K[A^+(R^1)(R^2)(R^3)]_p\}(X^-)_c(Y^-)_d$. $X^-$ is the same as $Y^-$ in the first ionic compound. $X^-$ is the same as $Y^-$ in the second ionic compound. $X^-$ in the first ionic compound is different from $X^-$ in the second ionic compound. $X^-$ differs from $Y^-$ in the third ionic compound. $X^-$ in the third ionic compound is the same as $X^-$ in the first ionic compound or $X^-$ in the second ionic compound. $Y^-$ in the third ionic compound is the same as $Y^-$ in the first ionic compound or $Y^-$ in the second ionic compound. A method for preparing an extracted material and a forward-osmosis water desalination system using the same are also provided.

22 Claims, 1 Drawing Sheet

(51) Int. Cl.
    *C07C 309/30*     (2006.01)
    *C02F 103/08*     (2006.01)

(56) References Cited

U.S. PATENT DOCUMENTS

| | | | |
|---|---|---|---|
| 10,016,725 B2 | 7/2018 | Liu et al. | |
| 2015/0273396 A1 | 10/2015 | Hancock et al. | |
| 2018/0008933 A1 | 1/2018 | Hu et al. | |
| 2018/0056241 A1* | 3/2018 | Liu | C07C 57/145 |
| 2018/0346496 A1* | 12/2018 | Chen | C07C 53/15 |

FOREIGN PATENT DOCUMENTS

| | | |
|---|---|---|
| TW | 201902908 A | 1/2019 |
| TW | I658045 B | 5/2019 |
| WO | WO 2011/097727 A1 | 8/2011 |
| WO | WO 2014/175834 A1 | 10/2014 |
| WO | WO 2015/147749 A1 | 10/2015 |
| WO | WO 2016/027280 A8 | 2/2016 |

OTHER PUBLICATIONS

Hsu et al., "Enhanced Forward Osmosis Desalination with a Hybrid Ionic Liquid/Hydrogel Thermoresponsive Draw Agent System," ACS Omega, vol. 4, 2019 (Published Feb. 27, 2019), pp. 4296-4303.

Taiwanese Office Action and Search Report for Taiwanese Application No. 109112136, dated Nov. 27, 2020.

* cited by examiner

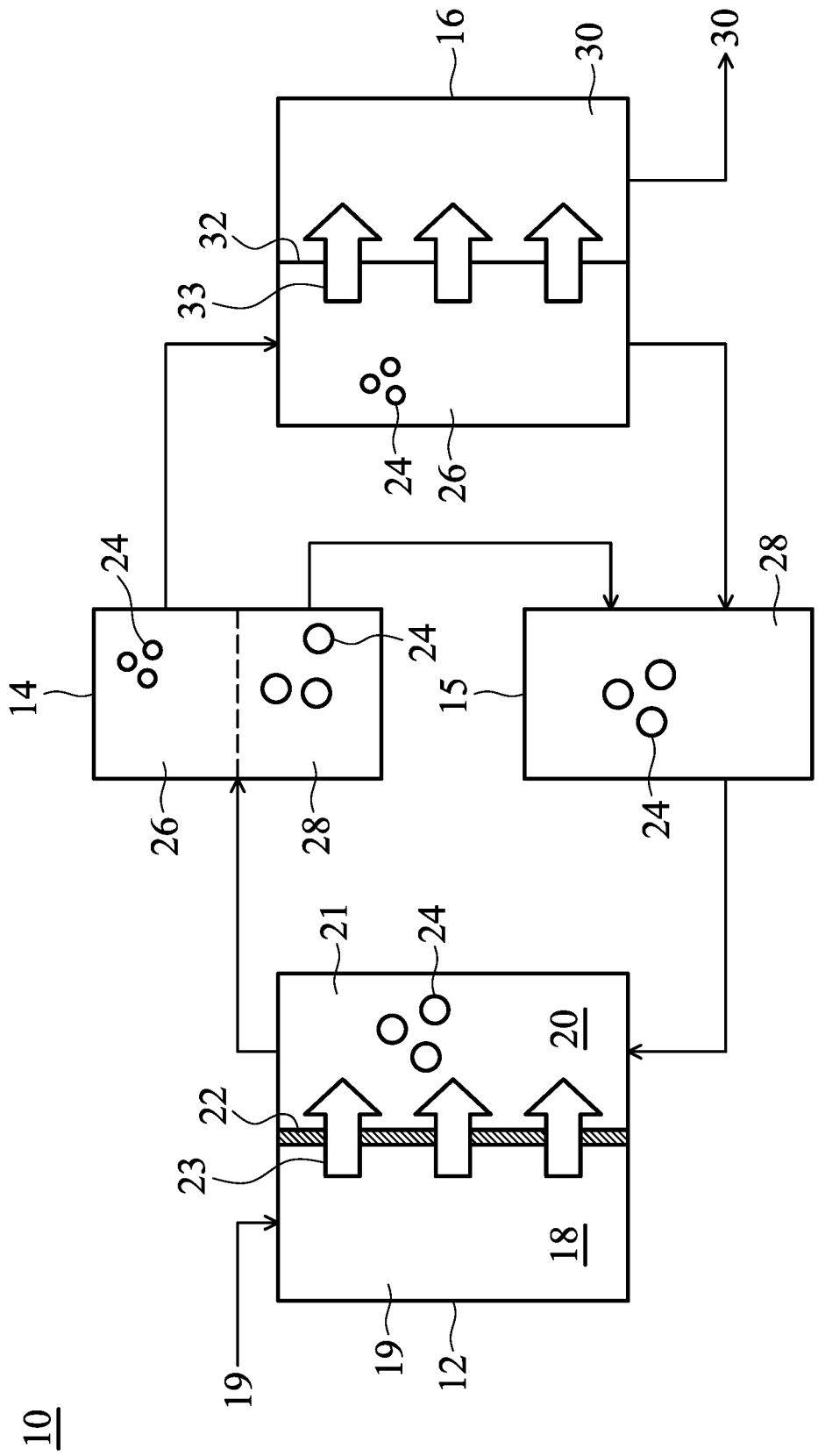

EXTRACTED MATERIAL FOR FORWARD OSMOSIS, PREPARATION METHOD THEREOF, AND FORWARD-OSMOSIS WATER DESALINATION SYSTEM USING THE SAME

TECHNICAL FIELD

The present disclosure relates to a blended-type extracted material for forward osmosis.

BACKGROUND

The forward-osmosis (FO) desalination technology uses the difference of osmotic pressure across a membrane as a driving force to attract water from a water-feeding end with low salinity (low osmotic pressure) to a draw-solution end with high salinity (high osmotic pressure). The draw solution diluted by water through the membrane is further recovered and concentrated to produce pure water by various separation methods.

The key to the forward-osmosis technology includes proper membranes, draw solution, and methods for separating the draw solution from pure water. In recent years, many industries have used temperature-sensitive materials as forward-osmosis draw solution to facilitate subsequent separation procedure, such as draw-solution materials having the characteristics of upper critical solution temperature (UCST) or lower critical solution temperature (LCST). This type of draw solution provides osmotic pressure during the forward-osmosis operation. After the forward-osmosis operation, the draw solution can be separated from water by temperature regulation. However, the separated aqueous solution still contains about 10-15% of the draw solution. This residual amount is not conducive to reducing the operating cost of the forward-osmosis system and affecting the quality of the produced water.

In order to achieve the best performance and lowest energy consumption of the system operation, the forward-osmosis operating system needs to adjust the characteristics of the extracted materials in time, such as the thermal-response temperature of the materials, the solute residual concentration in the water-rich phase, etc.

SUMMARY

In accordance with one embodiment of the present disclosure, an extracted material for forward osmosis is provided. The extracted material for forward osmosis includes a first ionic compound, a second ionic compound and a third ionic compound. The first ionic compound, the second ionic compound and the third ionic compound are represented by formula (I).

$$\{K[A^+(R^1)(R^2)(R^3)]_p\}(X^-)_c(Y^-)_d \qquad (I)$$

In formula (I), $R^1$, $R^2$ and $R^3$, independently, include straight or branched C1-12 alkyl, A includes phosphorus or nitrogen, K includes C1-15 alkyl and both ends thereof are connected to $[A^+(R^1)(R^2)(R^3)]$, p=2, c+d=2, and $X^-$ and $Y^-$ include $CH_3SO_3^-$, $I^-$, $CF_3COO^-$, $SCN^-$, $BF_4^-$, $CF_3SO_3^-$, $PF_6^-$, $FeCl_4^-$,

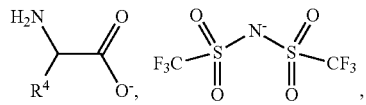

wherein $R^4$ is $-CH_2COOH$ or $-(CH_2)_4-NH_2$, $R^5$ and $R^6$ are H or $CH_3$, $R^7$ is $-CH(CH_3)_2$, $-(CH_2)_2-CH(CH_3)_2$, $-CH(CH_3)-CH_2-CH_3$ or $-CH_2-C_6H_5$, and $R^8$ is $CH_3$ or H. The group $X^-$ is the same as the group $Y^-$ in the first ionic compound. The group $X^-$ is the same as the group $Y^-$ in the second ionic compound. The group $X^-$ in the first ionic compound is different from the group $X^-$ in the second ionic compound. The group $X^-$ differs from the group $Y^-$ in the third ionic compound. The group $X^-$ in the third ionic compound is the same as the group $X^-$ in the first ionic compound or the group $X^-$ in the second ionic compound. The group $Y^-$ in the third ionic compound is the same as the group $Y^-$ in the first ionic compound or the group $Y^-$ in the second ionic compound.

In accordance with one embodiment of the present disclosure, a forward-osmosis water desalination system is provided. The forward-osmosis water desalination system includes a feeding unit, a phase-separation unit and a recovery unit. The feeding unit includes a feeding end and a draw-solution end. A semi-permeable membrane is used to separate the feeding end and the draw-solution end. The feeding end includes raw water. The draw-solution end includes an extracted material. The phase-separation unit is connected to the feeding unit. The phase-separation unit includes an aqueous layer and an ionic liquid layer. The concentration of the extracted material in the ionic liquid layer is greater than the concentration of the extracted material in the aqueous layer. The recovery unit is connected to the phase-separation unit and filters the aqueous layer to recover pure water.

In accordance with one embodiment of the present disclosure, a method for preparing an extracted material is provided. The preparation method includes providing a first ionic compound, providing a second ionic compound, and blending the first ionic compound and the second ionic compound to prepare an extracted material. The molar ratio of the first ionic compound to the second ionic compound is in a range from about 0.05:0.95 to about 0.95:0.05.

In order to achieve the best performance and minimum energy consumption of the forward osmosis (FO) system operation, the present disclosure quickly adjusts the characteristics of the extracted materials by simply mixing temperature-sensitive ionic compounds. Since the ion pairs in the ionic compounds have the characteristics of dissociation and re-pairing in water, the blended extracted materials are recombined to form a new formula composition, and this new formula composition has the effects of adjusting the phase-transition temperature of the extracted materials and reducing the residual amounts of the extracted materials in a water-rich phase.

A detailed description is given in the following embodiments with reference to the accompanying drawings.

BRIEF DESCRIPTION OF THE DRAWINGS

The present invention can be more fully understood by reading the subsequent detailed description and examples with references made to the accompanying drawings, wherein:

FIG. 1 is a schematic diagram of a forward-osmosis water desalination system in accordance with one embodiment of the present disclosure.

DETAILED DESCRIPTION

The following description is made for the purpose of illustrating the general principles of the invention and should not be taken in a limiting sense. The scope of the invention is best determined by reference to the appended claims.

In accordance with one embodiment of the present disclosure, an extracted material for forward osmosis is provided. The extracted material for forward osmosis includes a first ionic compound, a second ionic compound and a third ionic compound. The first ionic compound, the second ionic compound and the third ionic compound are represented by formula (I).

$$\{K[A^+(R^1)(R^2)(R^3)]_p\}(X^-)_c(Y^-)_d \qquad (I)$$

In formula (I), $R^1$, $R^2$ and $R^3$, independently, include straight or branched C1-12 alkyl, A includes phosphorus or nitrogen, K includes C1-15 alkyl and both ends thereof are connected to $[A^+(R^1)(R^2)(R^3)]$, p=2, c+d=2, and $X^-$ and $Y^-$ include $CH_3SO_3^-$, $I^-$, $CF_3COO^-$, $SCN^-$, $BF_4^-$, $CF_3SO_3^-$, $PF_6^-$, $FeCl_4^-$,

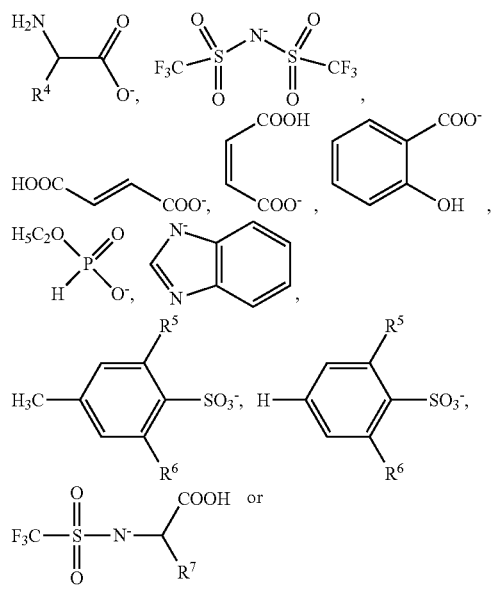

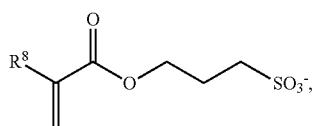

wherein $R^4$ is $—CH_2COOH$ or $—(CH_2)_4—NH_2$, $R^5$ and $R^6$ are H or $CH_3$, $R^7$ is $—CH(CH_3)_2$, $—(CH_2)_2—CH(CH_3)_2$, $—CH(CH_3)—CH_2—CH_3$ or $—CH_2—C_6H_5$, and $R^8$ is $CH_3$ or H. The group $X^-$ is the same as the group $Y^-$ in the first ionic compound. The group $X^-$ is the same as the group $Y^-$ in the second ionic compound. The group $X^-$ in the first ionic compound is different from the group $X^-$ in the second ionic compound. The group $X^-$ differs from the group $Y^-$ in the third ionic compound. The group $X^-$ in the third ionic compound is the same as the group $X^-$ in the first ionic compound or the group $X^-$ in the second ionic compound. The group $Y^-$ in the third ionic compound is the same as the group $Y^-$ in the first ionic compound or the group $Y^-$ in the second ionic compound.

In some embodiments, the first ionic compound and the second ionic compound may include

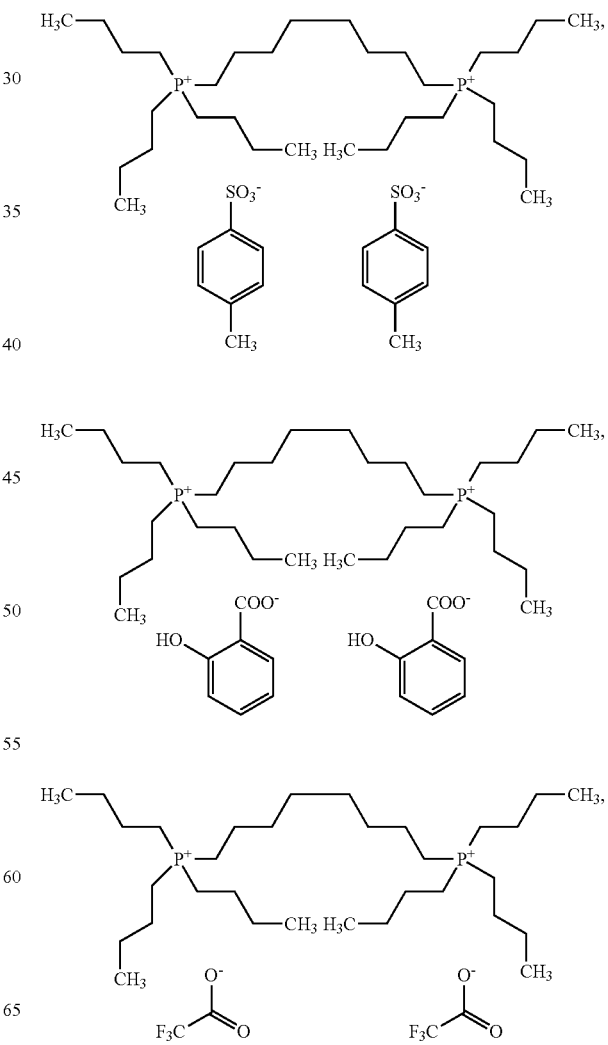

-continued

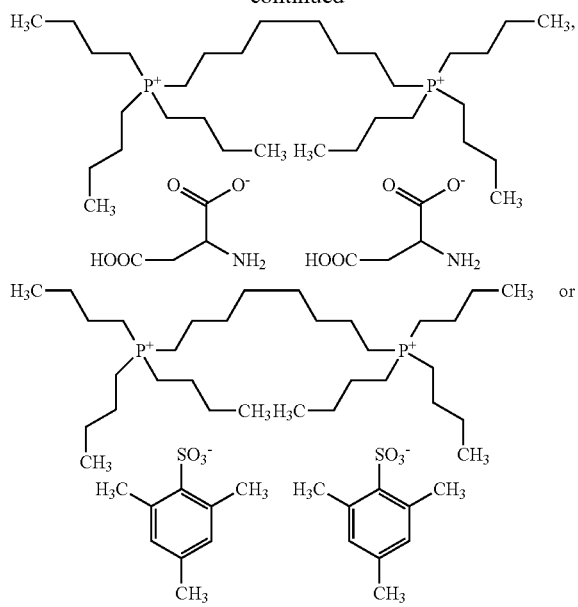

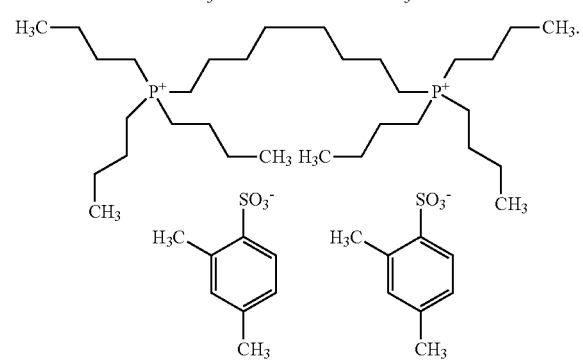

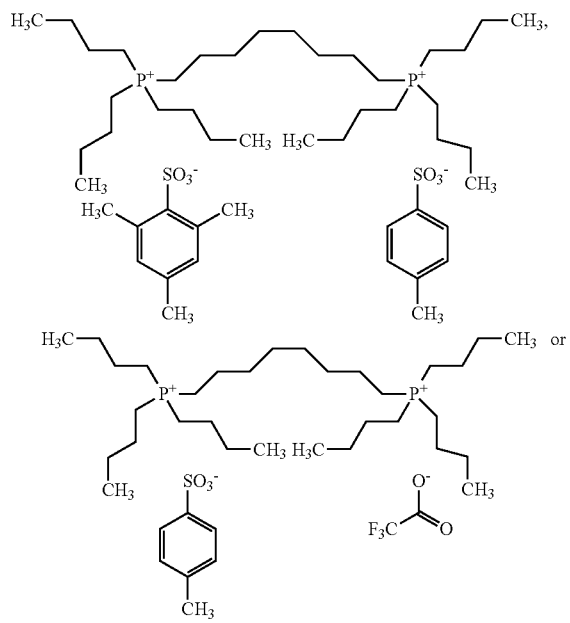

In some embodiments, the third ionic compound may include

-continued

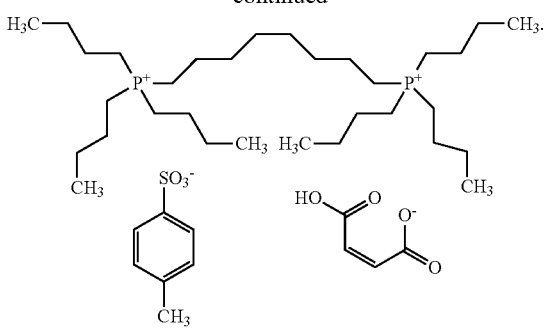

In some embodiments, the extracted material for forward osmosis further includes a fourth ionic compound which is represented by formula (II).

$$[A^+(R^1)(R^2)(R^3)(R^4)]_n(X^-)_a \qquad (II)$$

In formula (II), $R^1$, $R^2$, $R^3$ and $R^4$, independently, include straight or branched C1-12 alkyl, A includes phosphorus or nitrogen, n=1, a=1, and $X^-$ includes $CH_3SO_3^-$, $I^-$, $CF_3COO^-$, $SCN^-$, $BF_4^-$, $CF_3SO_3^-$, $PF_6^-$, $FeCl_4^-$,

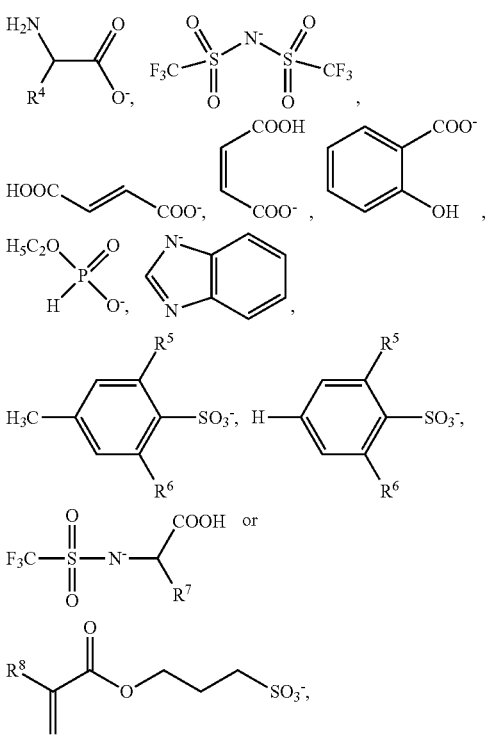

wherein $R^4$ is $-CH_2COOH$ or $-(CH_2)_4-NH_2$, $R^5$ and $R^6$ are H or $CH_3$, $R^7$ is $-CH(CH_3)_2$, $-(CH_2)_2-CH(CH_3)_2$, $-CH(CH_3)-CH_2-CH_3$ or $-CH_2-C_6H_5$, and $R^8$ is $CH_3$ or H.

In some embodiments, the fourth ionic compound may include

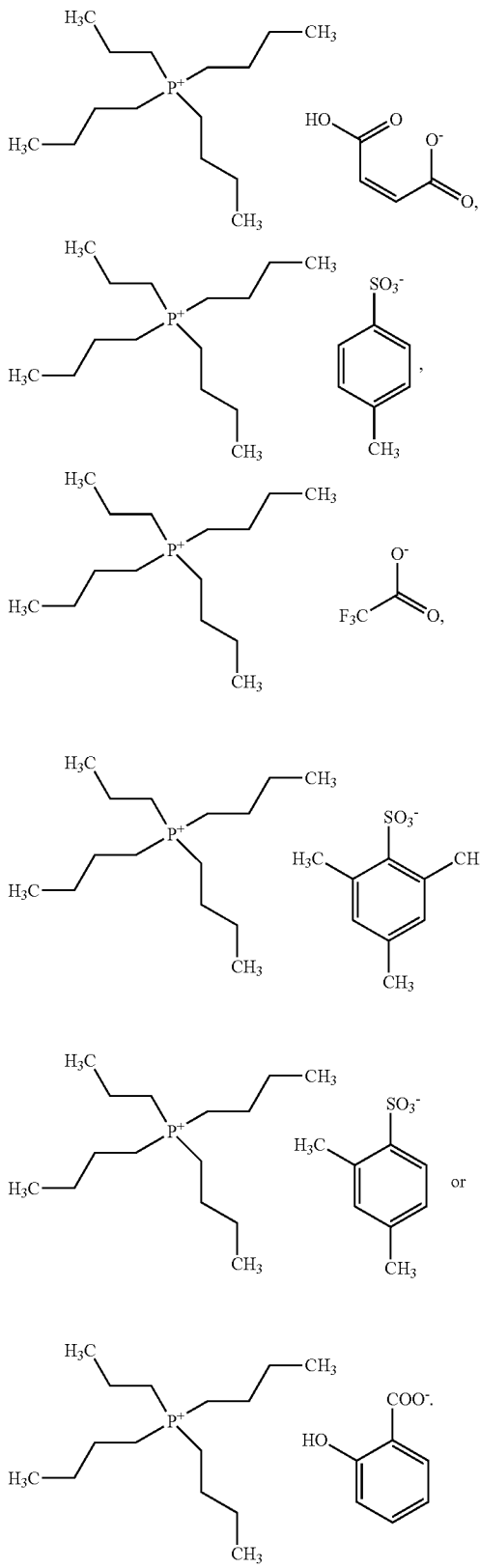

In some embodiments, the extracted material for forward osmosis further includes a fifth ionic compound which is represented by formula (III).

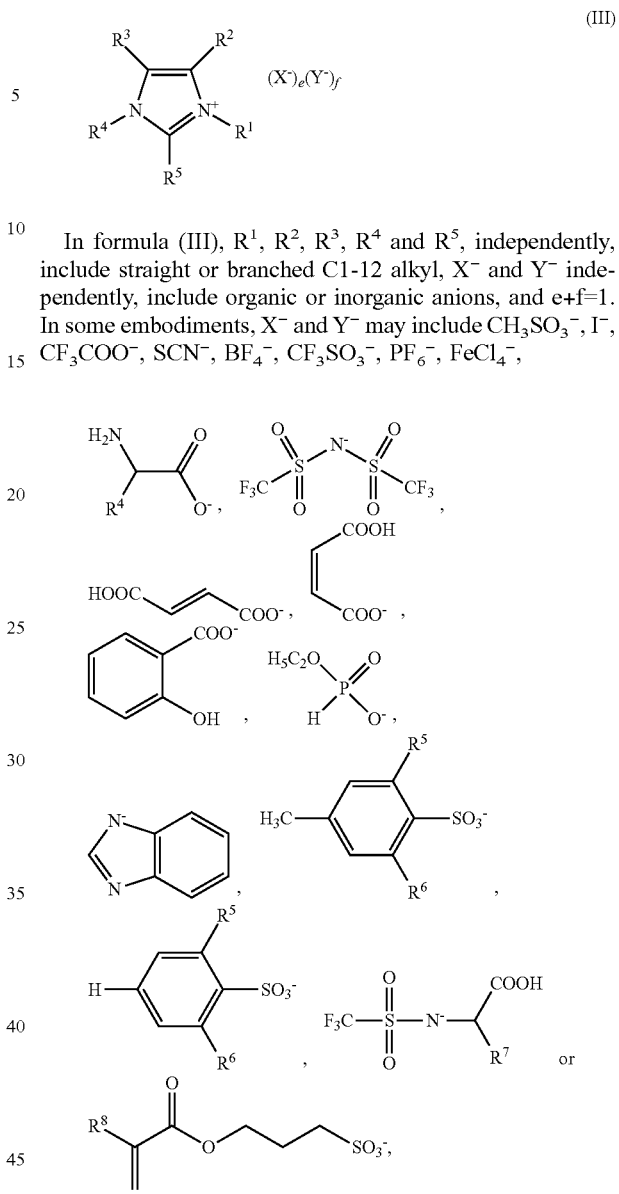

In formula (III), $R^1$, $R^2$, $R^3$, $R^4$ and $R^5$, independently, include straight or branched C1-12 alkyl, $X^-$ and $Y^-$ independently, include organic or inorganic anions, and e+f=1. In some embodiments, $X^-$ and $Y^-$ may include $CH_3SO_3^-$, $I^-$, $CF_3COO^-$, $SCN^-$, $BF_4^-$, $CF_3SO_3^-$, $PF_6^-$, $FeCl_4^-$, wherein $R^4$ is —$CH_2COOH$ or —$(CH_2)_4$—$NH_2$, $R^5$ and $R^6$ are H or $CH_3$, $R^7$ is —$CH(CH_3)_2$, —$(CH_2)_2$—$CH(CH_3)_2$, —$CH(CH_3)$—$CH_2$—$CH_3$ or —$CH_2$—$C_6H_5$, and $R^8$ is $CH_3$ or H.

In some embodiments, the phase-transition temperature of the extracted material is in a range from about 20° C. to about 50° C.

Referring to FIG. 1, in accordance with one embodiment of the present disclosure, a forward-osmosis water desalination system 10 is provided. FIG. 1 is a schematic diagram of the forward-osmosis water desalination system 10.

As shown in FIG. 1, the forward-osmosis water desalination system 10 includes a feeding unit 12, a phase-separation unit 14, a draw-solution tank 15 and a recovery unit 16. The feeding unit 12 is connected to the phase-separation unit 14. The phase-separation unit 14 is connected to the draw-solution tank 15 and the recovery unit 16. The draw-solution tank 15 is connected to the feeding unit 12. The recovery unit 16 is connected to the draw-solution tank 15. The feeding unit 12 includes a feeding end 18 and a draw-solution end 20. A semi-permeable membrane 22 is used to separate the feeding end 18 and the draw-solution end 20. The feeding end 18 includes raw water 19. The draw-solution end 20 includes an extracted material 24. The phase-separation unit 14 includes an aqueous layer 26 and an ionic liquid layer 28. The concentration of the extracted material 24 in the ionic liquid layer 28 is greater than the concentration of the extracted material 24 in the aqueous layer 26. The recovery unit 16 filters the aqueous layer 26 to obtain pure water 30. In some embodiments, the raw water 19 may include brine, seawater, wastewater or drug/food concentrates.

In some embodiments, the extracted material 24 includes a first ionic compound, a second ionic compound and a third ionic compound. The first ionic compound, the second ionic compound and the third ionic compound are represented by formula (I).

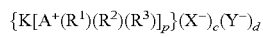  (I)

In formula (I), $R^1$, $R^2$ and $R^3$, independently, include straight or branched C1-12 alkyl, A includes phosphorus or nitrogen, K includes C1-15 alkyl and both ends thereof are connected to $[A^+(R^1)(R^2)(R^3)]$, p=2, c+d=2, and $X^-$ and $Y^-$ include $CH_3SO_3^-$, $I^-$, $CF_3COO^-$, $SCN^-$, $BF_4^-$, $CF_3SO_3^-$, $PF_6^-$, $FeCl_4^-$,

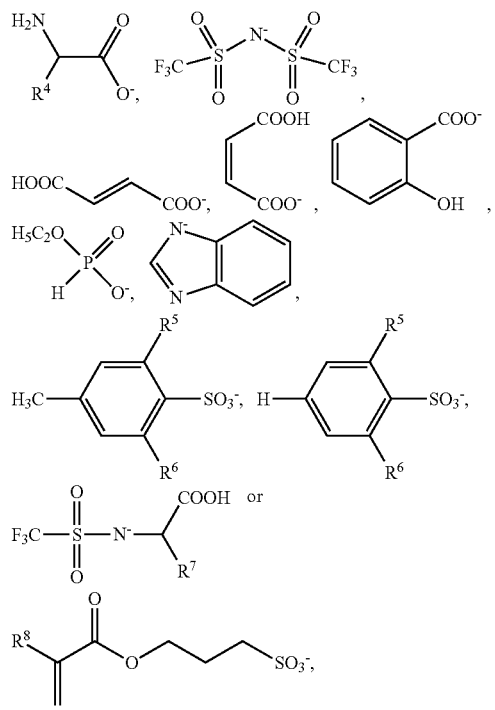

wherein $R^4$ is —$CH_2COOH$ or —$(CH_2)_4$—$NH_2$, $R^5$ and $R^6$ are H or $CH_3$, $R^7$ is —$CH(CH_3)_2$, —$(CH_2)_2$—$CH(CH_3)_2$, —$CH(CH_3)$—$CH_2$—$CH_3$ or —$CH_2$—$C_6H_5$, and $R^8$ is $CH_3$ or H. The group $X^-$ is the same as the group $Y^-$ in the first ionic compound. The group $X^-$ is the same as the group $Y^-$ in the second ionic compound. The group $X^-$ in the first ionic compound is different from the group $X^-$ in the second ionic compound. The group $X^-$ differs from the group $Y^-$ in the third ionic compound. The group $X^-$ in the third ionic compound is the same as the group $X^-$ in the first ionic compound or the group $X^-$ in the second ionic compound.

The group $Y^-$ in the third ionic compound is the same as the group $Y^-$ in the first ionic compound or the group $Y^-$ in the second ionic compound.

In some embodiments, the first ionic compound and the second ionic compound may include

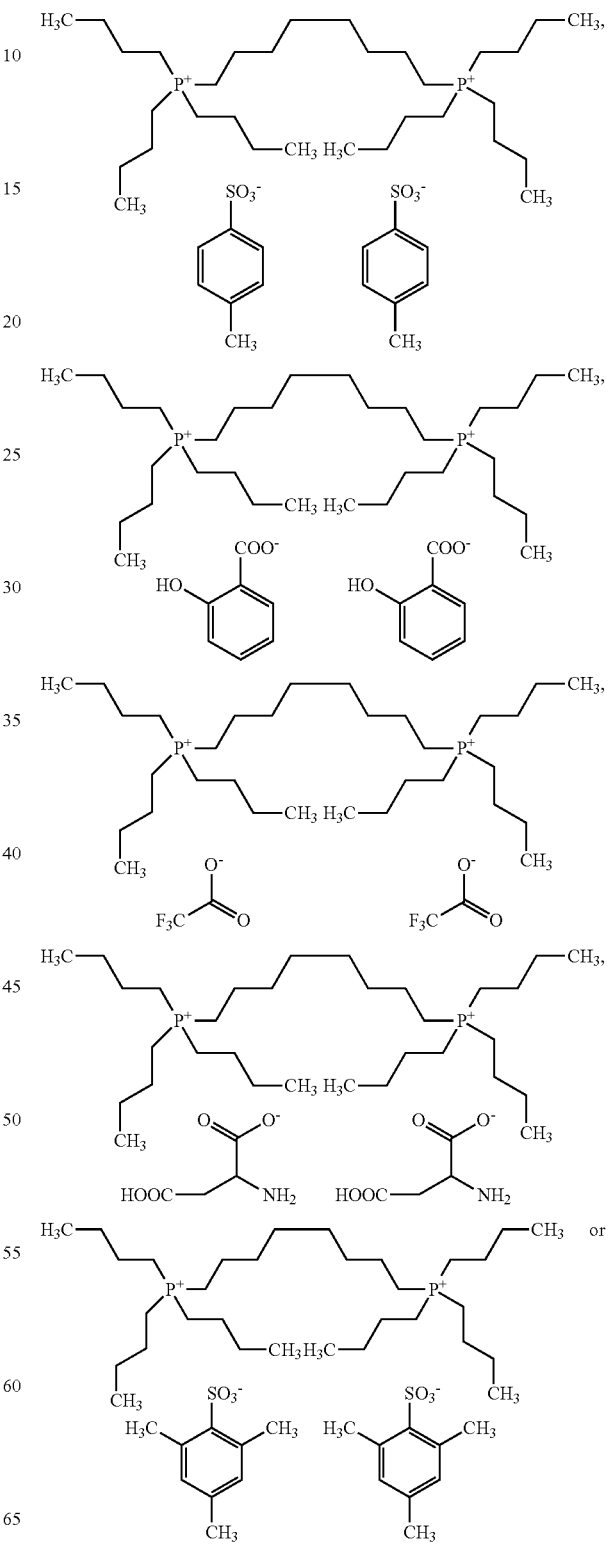

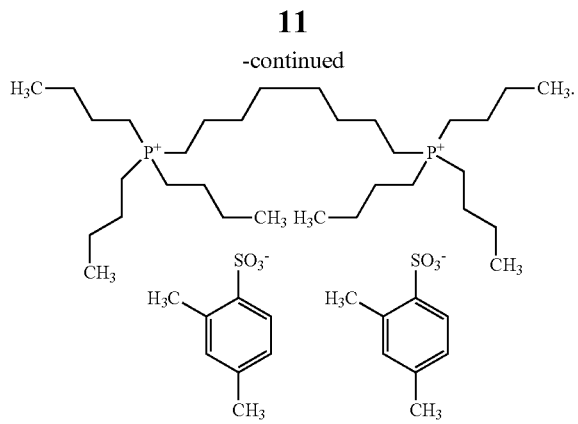

In some embodiments, the third ionic compound may include

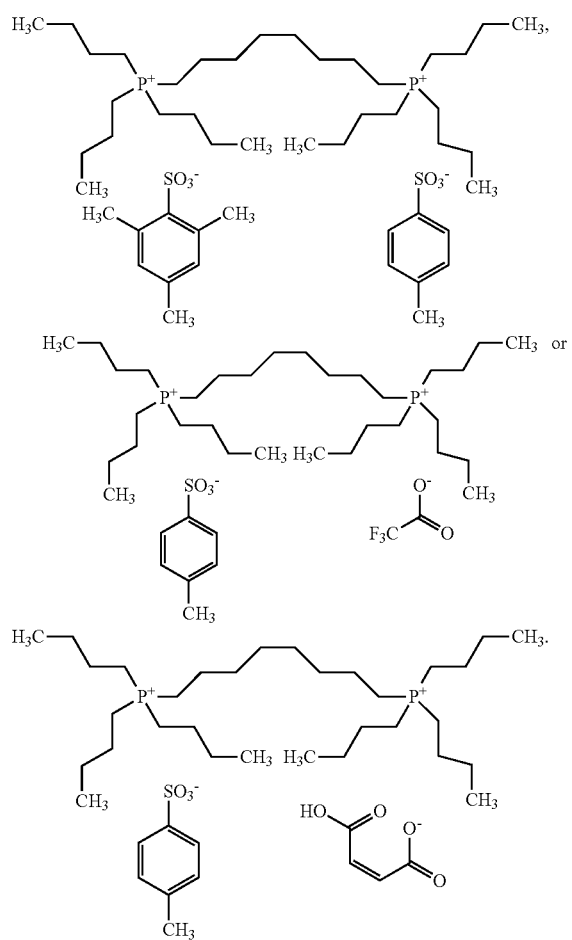

In some embodiments, the extracted material 24 further includes a fourth ionic compound which is represented by formula (II).

$$[A^+(R^1)(R^2)(R^3)(R^4)]_n(X^-)_a \quad (II)$$

In formula (II), $R^1$, $R^2$, $R^3$ and $R^4$, independently, include straight or branched C1-12 alkyl, A includes phosphorus or nitrogen, n=1, a=1, and $X^-$ includes $CH_3SO_3^-$, $I^-$, $CF_3COO^-$, $SCN^-$, $BF_4^-$, $CF_3SO_3^-$, $PF_6^-$, $FeCl_4^-$,

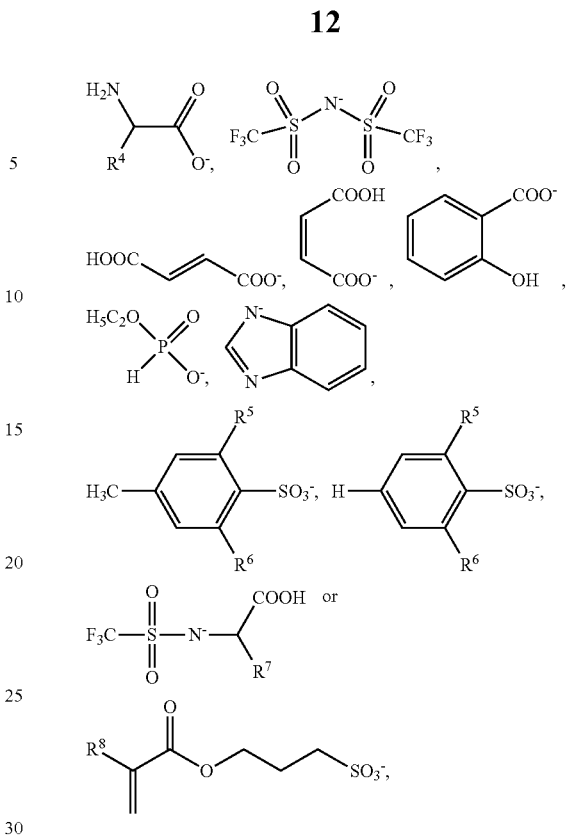

wherein $R^4$ is $—CH_2COOH$ or $—(CH_2)_4—NH_2$, $R^5$ and $R^6$ are H or $CH_3$, $R^7$ is $—CH(CH_3)_2$, $—(CH_2)_2—CH(CH_3)_2$, $—CH(CH_3)—CH_2—CH_3$ or $—CH_2—C_6H_5$, and $R^8$ is $CH_3$ or H.

In some embodiments, the fourth ionic compound may include

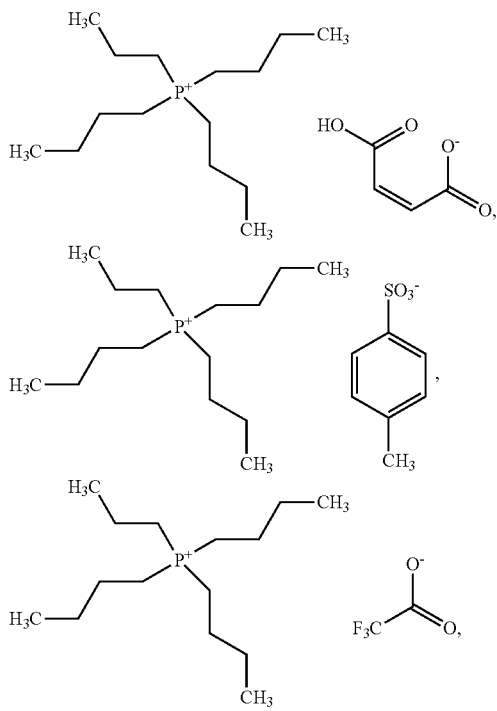

-continued

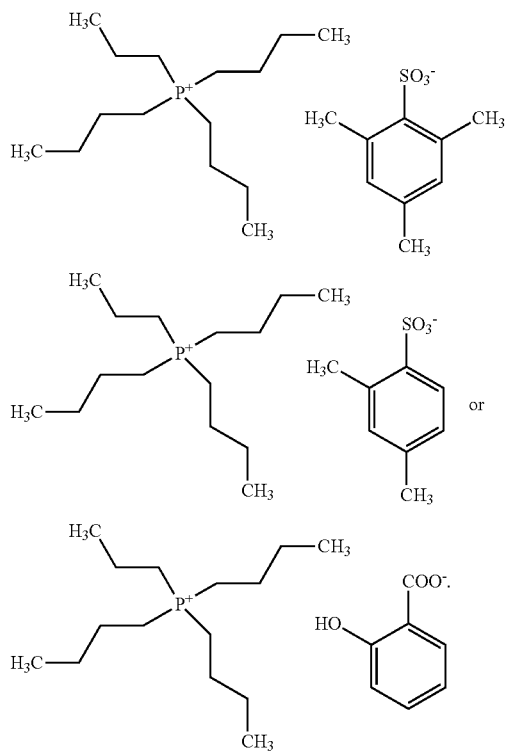

In some embodiments, the extracted material 24 further includes a fifth ionic compound which is represented by formula (III).

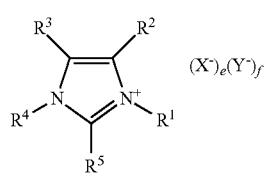
(III)

In formula (III), $R^1$, $R^2$, $R^3$, $R^4$ and $R^5$, independently, include straight or branched C1-12 alkyl, $X^-$ and $Y^-$ independently, include organic or inorganic anions, and e+f=1. In some embodiments, $X^-$ and $Y^-$ may include $CH_3SO_3^-$, $I^-$, $CF_3COO^-$, $SCN^-$, $BF_4^-$, $CF_3SO_3^-$, $PF_6^-$, $FeCl_4^-$,

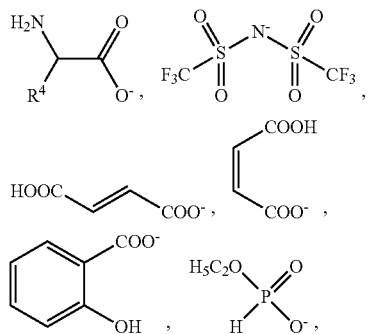

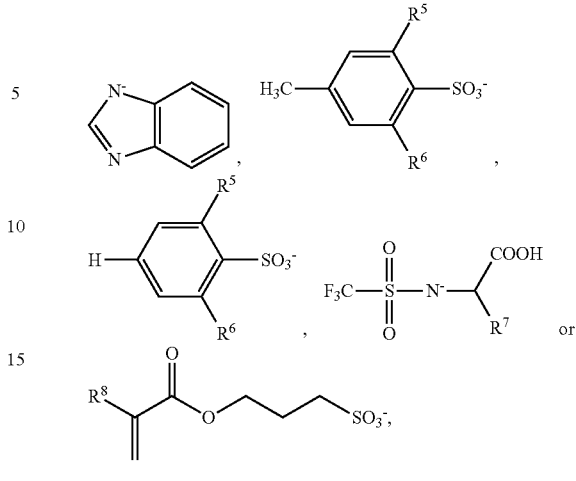

wherein $R^4$ is $-CH_2COOH$ or $-(CH_2)_4-NH_2$, $R^5$ and $R^6$ are H or $CH_3$, $R^7$ is $-CH(CH_3)_2$, $-(CH_2)_2-CH(CH_3)_2$, $-CH(CH_3)-CH_2-CH_3$ or $-CH_2-C_6H_5$, and $R^8$ is $CH_3$ or H.

In some embodiments, the phase-transition temperature of the extracted material is in a range from about 20° C. to about 50° C.

In some embodiments, in the phase-separation unit 14, the concentration of the extracted material 24 is less than about 10% in the aqueous layer 26. In some embodiments, in the phase-separation unit 14, the concentration of the extracted material 24 is in a range from about 10% to about 70% in the ionic liquid layer 28. In some embodiments, the operating temperature of the phase-separation unit 14 is in a range from about 20° C. to about 50° C. In some embodiments, the recovery unit 16 further includes a thin film 32 which is used to filter the aqueous layer 26 introduced from the phase-separation unit 14 to obtain pure water 30. In some embodiments, the thin film 32 may include an ultrafiltration (UF) thin film, a nanofiltration (NF) thin film or a reverse osmosis (RO) thin film.

Referring to FIG. 1, the operation process of the forward-osmosis water desalination system 10 is further illustrated. The raw water 19 is introduced into the feeding end 18 of the feeding unit 12. The ionic liquid 21 containing the extracted material 24 is introduced into the draw-solution end 20 of the feeding unit 12. At this time, water molecules in the raw water 19 pass through the semi-permeable membrane 22 into the draw-solution end 20 in an osmotic manner 23 due to the difference of osmotic pressure on the both sides of the semi-permeable membrane 22, and are mixed with the ionic liquid 21 to form a draw solution. The draw solution continues to enter the phase-separation unit 14. At a specific temperature, for example 20-50° C., the draw solution is separated into an aqueous layer 26 and an ionic liquid layer 28. At this time, the concentration of the extracted material 24 in the ionic liquid layer 28 is greater than the concentration of the extracted material 24 in the aqueous layer 26. The aqueous layer 26 and the ionic liquid layer 28 in the phase-separation unit 14 continue to flow to different units. The aqueous layer 26 enters the recovery unit 16. The ionic liquid layer 28 containing the high-concentration extracted material 24 enters the draw-solution tank 15, and then returns to the draw-solution end 20 of the feeding unit 12. The recovery unit 16 performs a filtering step 33 on the introduced aqueous layer 26 through the thin film 32 to obtain pure water 30. The extracted material 24 in the aqueous layer 26 enters the draw-solution tank 15 and then flows back to the draw-solution end 20 of the feeding unit 12.

In accordance with one embodiment of the present disclosure, a method for preparing an extracted material is provided. The preparation method includes providing a first ionic compound, providing a second ionic compound, and blending the first ionic compound and the second ionic compound to prepare an extracted material. The molar ratio of the first ionic compound to the second ionic compound is in a range from about 0.05:0.95 to about 0.95:0.05, for example, from about 0.15:0.85 to about 0.85:0.15, from about 0.25:0.75 to about 0.75:0.25, from about 0.33:0.67 to about 0.67:0.33, about 0.15:0.85, about 0.20:0.80, about 0.3:0.7, about 0.4:0.6, about 0.5:0.5, about 0.6:0.4, about 0.7:0.3, about 0.85:0.15, etc., but not limited to this. The first ionic compound and the second ionic compound are represented by formula (I).

$$\{K[A^+(R^1)(R^2)(R^3)]_p\}(X^-)_c(Y^-)_d \quad (I)$$

In formula (I), $R^1$, $R^2$ and $R^3$, independently, include straight or branched C1-12 alkyl, A includes phosphorus or nitrogen, K includes C1-15 alkyl and both ends thereof are connected to $[A^+(R^1)(R^2)(R^3)]$, p=2, c+d=2, and $X^-$ and $Y^-$ include $CH_3SO_3^-$, $I^-$, $CF_3COO^-$, $SCN^-$, $BF_4^-$, $CF_3SO_3^-$, $PF_6^-$, $FeCl_4^-$,

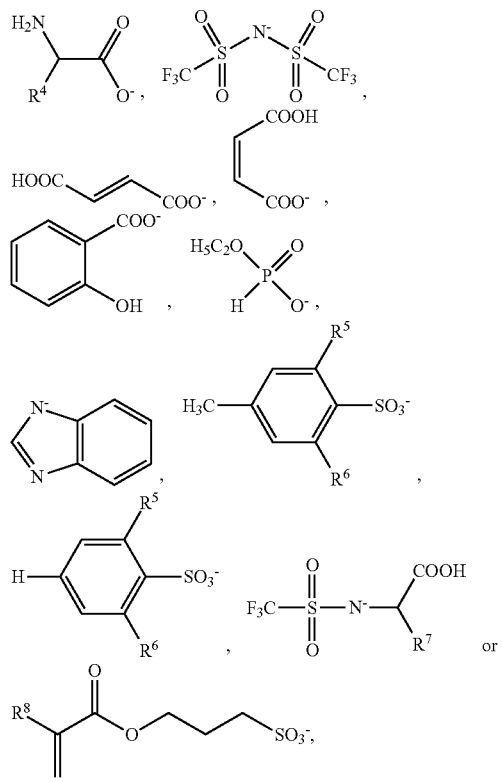

wherein $R^4$ is —$CH_2COOH$ or —$(CH_2)_4$—$NH_2$, $R^5$ and $R^6$ are H or $CH_3$, $R^7$ is —$CH(CH_3)_2$, —$(CH_2)_2$—$CH(CH_3)_2$, —$CH(CH_3)$—$CH_2$—$CH_3$ or —$CH_2$—$C_6H_5$, and $R^8$ is $CH_3$ or H.

In some embodiments, the first ionic compound and the second ionic compound may include

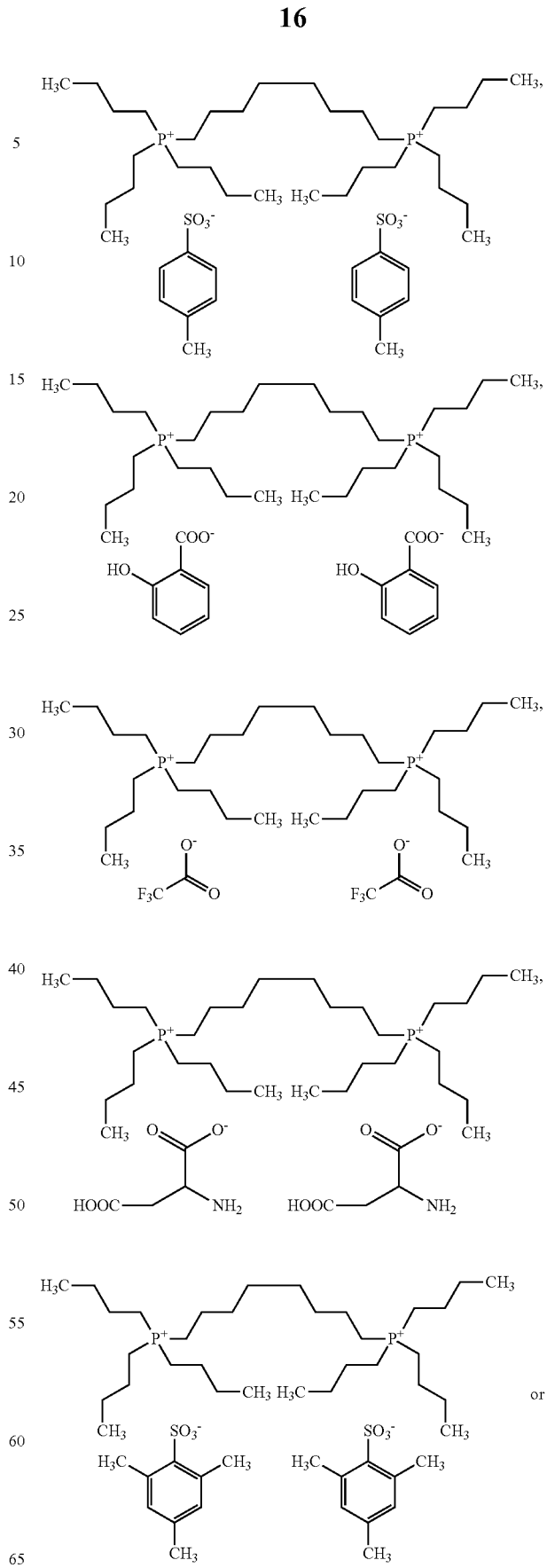

-continued

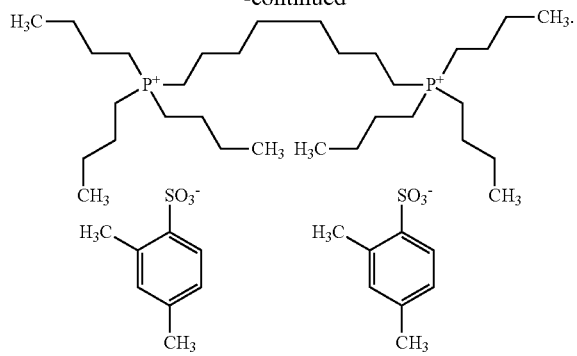

In some embodiments, the molar ratio of the first ionic compound to the second ionic compound is in a range from about 0.15:0.85 to about 0.85:0.15, for example, from about 0.25:0.75 to about 0.75:0.25, from about 0.33:0.67 to about 0.67:0.33, about 0.3:0.7, about 0.4:0.6, about 0.5:0.5, about 0.6:0.4, about 0.7:0.3, etc., but not limited to this.

In some embodiments, the method for preparing an extracted material further includes blending a fourth ionic compound which is represented by formula (II).

$$[A^+(R^1)(R^2)(R^3)(R^4)]_n(X^-)_a \qquad (II)$$

In formula (II), $R^1$, $R^2$, $R^3$ and $R^4$, independently, include straight or branched C1-12 alkyl, A includes phosphorus or nitrogen, n=1, a=1, and $X^-$ includes $CH_3SO_3^-$, $I^-$, $CF_3COO^-$, $SCN^-$, $BF_4^-$, $CF_3SO_3^-$, $PF_6^-$, $FeCl_4^-$,

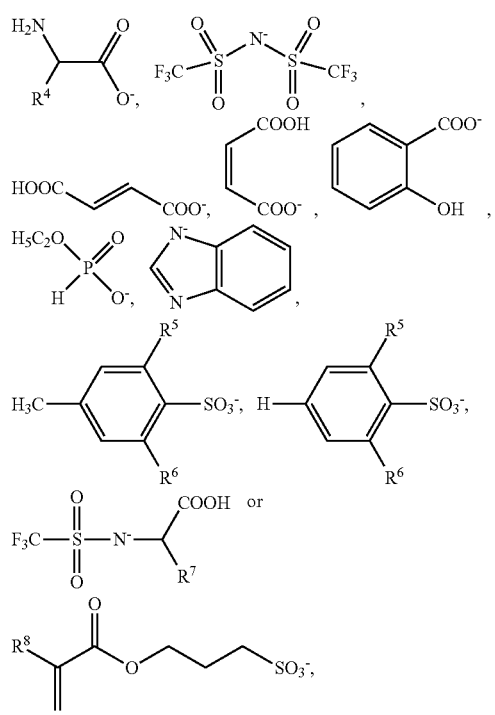

wherein $R^4$ is —$CH_2COOH$ or —$(CH_2)_4$—$NH_2$, $R^5$ and $R^6$ are H or $CH_3$, $R^7$ is —$CH(CH_3)_2$, —$(CH_2)_2$—$CH(CH_3)_2$, —$CH(CH_3)$—$CH_2$—$CH_3$ or —$CH_2$—$C_6H_5$, and $R^8$ is $CH_3$ or H.

In some embodiments, the fourth ionic compound may include

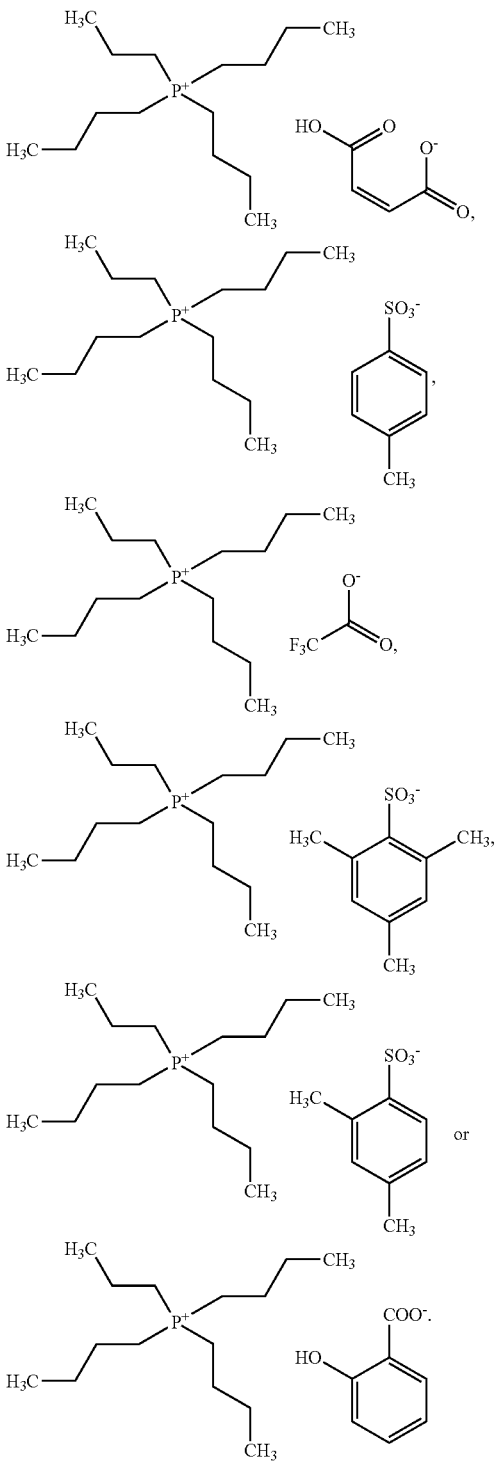

In some embodiments, the molar ratio of the first ionic compound to the second ionic compound to the fourth ionic compound is about 0.05-0.90:0.05-0.90:0.05-0.90, for example, about 0.10-0.80:0.10-0.80:0.10-0.80, about 0.15-0.70:0.15-0.70:0.15-0.70, about 0.20-0.60:0.20-0.60:0.20-0.60, about 0.10:0.10:0.80, about 0.10:0.15:0.75, about 0.15:0.15:0.70, about 0.20:0.10:0.70, about 0.20:0.20:0.60, about 0.30:0.20:0.50, about 0.30:0.30:0.4, about 0.40:0.30:0.30, about 0.50:0.30:0.20, about 0.60:0.20:0.20, about 0.70:0.10:0.20, about 0.75:0.15:0.10, about 0.80:0.10:0.10, etc., but not limited to this. In some embodiments, the molar ratio of the first ionic compound to the second ionic compound to the fourth ionic compound is about 0.10-0.80:0.10-0.80:0.10-0.80, for example, about 0.15-0.70:0.15-0.70: 0.15-0.70, about 0.20-0.60:0.20-0.60:0.20-0.60, about 0.30-0.40:0.30-0.40:0.30-0.40, about 0.15:0.15:0.70, about 0.20:0.20:0.60, about 0.30:0.20:0.50, about 0.30:0.30:0.4, about 0.40:0.30:0.30, about 0.50:0.30:0.20, about 0.60:0.20:0.20, etc., but not limited to this.

In some embodiments, the method for preparing an extracted material further includes blending a fifth ionic compound which is represented by formula (III).

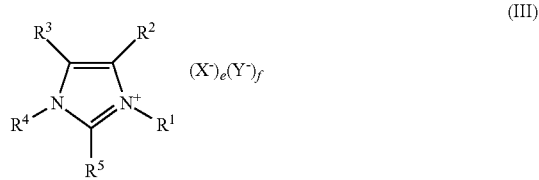

In formula (III), $R^1$, $R^2$, $R^3$, $R^4$ and $R^5$, independently, include straight or branched C1-12 alkyl, $X^-$ and $Y^-$, independently, include organic or inorganic anions, and e+f=1. In some embodiments, $X^-$ and $Y^-$ may include $CH_3SO_3^-$, $I^-$, $CF_3COO^-$, $SCN^-$, $BF_4^-$, $CF_3SO_3^-$, $PF_6^-$, $FeCl_4^-$,

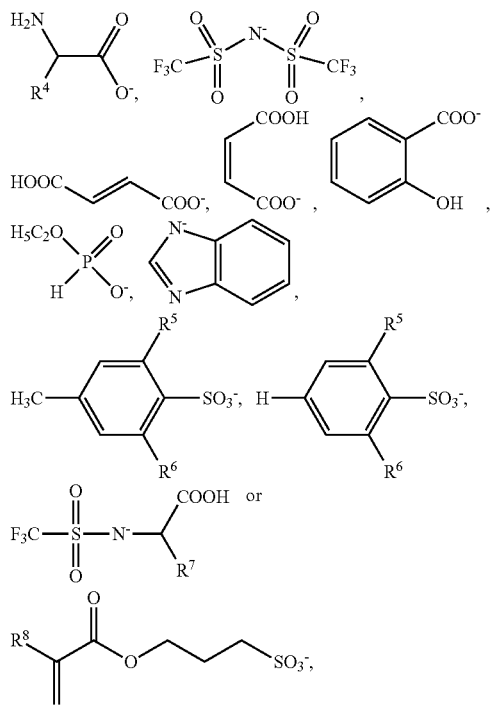

wherein $R^4$ is $-CH_2COOH$ or $-(CH_2)_4-NH_2$, $R^5$ and $R^6$ are H or $CH_3$, $R^7$ is $-CH(CH_3)_2$, $-(CH_2)_2-CH(CH_3)_2$, $-CH(CH_3)-CH_2-CH_3$ or $-CH_2-C_6H_5$, and $R^8$ is $CH_3$ or H.

In some embodiments, the molar ratio of the first ionic compound to the second ionic compound to the fifth ionic compound is about 0.05-0.90:0.05-0.90:0.05-0.90, for example, about 0.10-0.80:0.10-0.80:0.10-0.80, about 0.15-0.70:0.15-0.70:0.15-0.70, about 0.20-0.60:0.20-0.60:0.20-0.60, about 0.10:0.10:0.80, about 0.10:0.15:0.75, about 0.15:0.15:0.70, about 0.20:0.10:0.70, about 0.20:0.20:0.60, about 0.30:0.20:0.50, about 0.30:0.30:0.4, about 0.40:0.30:0.30, about 0.50:0.30:0.20, about 0.60:0.20:0.20, about 0.70:0.10:0.20, about 0.75:0.15:0.10, about 0.80:0.10:0.10, etc., but not limited to this. In some embodiments, the molar ratio of the first ionic compound to the second ionic compound to the fifth ionic compound is about 0.10-0.80:0.10-0.80:0.10-0.80, for example, about 0.15-0.70:0.15-0.70: 0.15-0.70, about 0.20-0.60:0.20-0.60:0.20-0.60, about 0.30-0.40:0.30-0.40:0.30-0.40, about 0.15:0.15:0.70, about 0.20: 0.20:0.60, about 0.30:0.20:0.50, about 0.30:0.30:0.4, about 0.40:0.30:0.30, about 0.50:0.30:0.20, about 0.60:0.20:0.20, etc., but not limited to this.

In some embodiments, the phase-transition temperature of the extracted material is in a range from about 20° C. to about 50° C.

In order to achieve the best performance and minimum energy consumption of the forward osmosis (FO) system operation, the present disclosure quickly adjusts the characteristics of the extracted materials by simply mixing temperature-sensitive ionic compounds. Since the ion pairs in the ionic compounds have the characteristics of dissociation and re-pairing in water, the blended extracted materials are recombined to form a new formula composition, and this new formula composition has the effects of adjusting the phase-transition temperature of the extracted materials and reducing the residual amounts of the extracted materials in a water-rich phase.

Example 1

Preparation of Blended-Type Extracted Materials (1) Preparation of 1,8-octanediyl-bis(tri-n-butylphosphonium)di(p-toluenesulfonate)(P2-TOS)

First, 1,8-octanediyl-bis(tri-n-butylphosphonium)dibromide (P2-Br) was synthesized by the following steps.

80 g of tributylphosphine (0.4 mol), 48.9 g of 1,8-dibromooctane (0.18 mol), and 150 mL of acetone were placed in a 500-mL round-bottomed reaction flask and stirred with a magnet at 40° C. for 48 hours. After the reaction, the above solution was slowly dropped into 1.5 L of ether. After filtration, white powdery solid was obtained and washed several times with ether. The washed white solid was dried under vacuum to obtain 117 g of product P2-Br.

Next, 1,8-octanediyl-bis(tri-n-butylphosphonium)di(p-toluenesulfonate) (P2-TOS) was synthesized by the following steps.

First, P2-Br was converted to P2-OH (1,8-octanediyl-bis (tri-n-butylphosphonium)dihydroxide) with an ion-exchange resin. 266.87 g of P2-OH with a concentration of 30.9% (0.15 mol) and 57.07 g of p-Toluenesulfonic acid monohydrate (0.3 mol) were dissolved in 300 g of deionized water and stirred at room temperature for 12 hours. After the reaction, 300 mL of ethyl acetate was added for extraction and repeated twice. The washed organic layer was concentrated in vacuum at 30° C. to obtain about 116 g of product P2-TOS. The product P2-TOS was determined by NMR ($^1$H-NMR, 500 MHz in D2O): 0.81 (t, 18H, CH3CH2-), 1.09 (m, 4H, —CH2-), 1.1-1.5 (m, 32H, —CH2-), 1.9-2.1 (t, 16H, PCH2-), 2.25 (s, 6H, Ar—CH3), 7.21 (d, 4H, ArH), 7.58 (d, 4H, ArH).

(2) Preparation of 1,8-octanediyl-bis(tri-n-butylphosphonium)di(2,4,6-trimethyl-benzenesulfonate) (P2-TMBS)

1,8-octanediyl-bis(tri-n-butylphosphonium)di(2,4,6-trimethyl-benzenesulfonate) (P2-TMBS) was synthesized by the following steps.

First, P2-Br was converted to P2-OH (1,8-octanediyl-bis(tri-n-butylphosphonium)dihydroxide) with an ion-exchange resin. 498.20 g of P2-OH with a concentration of 30.9% (0.28 mol) and 132.32 g of 2-Mesitylenesulfonic acid dihydrate (0.56 mol) were dissolved in 700 g of deionized water and stirred at room temperature for 12 hours. After the reaction, 500 mL of ethyl acetate was added for extraction once, and the upper ethyl acetate layer was collected. The organic layer was concentrated in vacuum at 30° C. to obtain about 244 g of product P2-TMBS. The product P2-TMBS was determined by NMR ($^1$H-NMR, 500 MHz in D2O): 0.8 (t, 18H, CH3CH2-), 1.09 (m, 4H, —CH2-), 1.1-1.5 (m, 32H, —CH2-), 1.9-2.0 (t, 16H, PCH2-), 2.12 (s, 6H, Ar—CH3), 2.25 (s, 12H, Ar—CH3), 6.88 (s, 4H, ArH).

(3) Blending of P2-TOS and P2-TMBS

P2-TOS and P2-TMBS ionic compounds of two different structures were selected for blending, and the blending ratios (molar ratios) were 1:0.67, 1:1, and 1:2, respectively, as shown in Table 1.

TABLE 1

| | | P2-TOS:P2-TMBS blending (molar ratios) | | |
|---|---|---|---|---|
| | | 1:0.67 | 1:1 | 1:2 |
| P2-TOS | mole number (mmole) | 11.4 | 7.6 | 4.35 |
| | weight (g) | 9.8 | 6.5 | 3.7 |
| P2-TMBS | mole number (mmole) | 7.6 | 7.6 | 8.7 |
| | weight (g) | 7.0 | 7.0 | 8.0 |

Example 2

Verification of Characteristics of Blended-Type Extracted Materials

A test of phase-transition temperature and a test of osmotic pressure were performed on the extracted materials of P2-TOS, the extracted materials of P2-TMBS, and the extracted materials of P2-TOS and P2-TMBS with different blending ratios. The results of the test of phase-transition temperature are shown in Table 2. Table 2 shows a comparison of the phase-transition temperature of the extracted materials of P2-TOS, the extracted materials of P2-TMBS, and the extracted materials of P2-TOS and P2-TMBS with different blending ratios at different concentrations. The above materials were homogeneous at room temperature (25° C.), and phase separation began to occur after increasing the temperature. The material of P2-TOS had more hydrophilicity than that of P2-TMBS, and the phase separation of P2-TOS occurred at higher temperatures. For the extracted materials of P2-TOS and P2-TMBS with different blending ratios, the phase-transition temperature thereof was between those of P2-TOS and P2-TMBS, and as the blending ratio of P2-TOS decreased, the phase-transition temperature also dropped slightly. From the results in Table 2, it can be verified that the blended-type extracted materials of the present disclosure produce phase separation at low temperature.

TABLE 2

| | phase-transition temperature (° C.) | | | | |
|---|---|---|---|---|---|
| concentration (%) | P2-TOS | P2-TOS:P2-TMBS (blending molar ratio) | | | P2-TMBS |
| | | 1:0.67 | 1:1 | 1:2 | |
| 5% | 66 | 38 | 40 | 36 | 25 |
| 10% | 44 | 29 | 28 | 25 | 21 |
| 20% | 36 | 27 | 26 | 23 | 20 |
| 30% | 35 | x | x | x | 20 |
| 50% | 38 | 29 | 28 | 25 | x |
| 60% | 52 | 33 | 31 | 28 | 23 |
| 70% | no phase separation | no phase separation | no phase separation | 49 | 32 |
| 80% | no phase separation | no phase separation | no phase separation | no phase separation | no phase separation | note:
x no measurement

In addition, the osmotic pressure of the extracted materials of P2-TOS, the extracted materials of P2-TMBS, and the extracted materials of P2-TOS and P2-TMBS with different blending ratios at different concentrations was analyzed by the freezing point depression method, as shown in Table 3. When P2-TOS and P2-TMBS were blended at a ratio of 1:1 (molar ratio), the osmotic pressure value at a concentration of 50% was 3.534 osmol/kg, which was about three times that of seawater. When P2-TOS and P2-TMBS were blended at a ratio of 1:2 (molar ratio), the osmotic pressure value at a concentration of 50% was 2.775 osmol/kg, which was about 2.3 times that of seawater. When P2-TOS was blended with P2-TMBS, taking the blending ratio of 1:2 as an example, at a concentration of 50%, the osmotic pressure of the blended material still reached about 0.76 times of that of pure P2-TOS. It is shown that the disclosed blended-type extracted materials have considerable ability to extract water.

TABLE 3

| | | P2-TOS:P2-TMBS (Osmol/kg) | | |
|---|---|---|---|---|
| concentration | P2-TOS (Osmol/kg) | 1:1 (mole ratio) | 1:2 (mole ratio) | P2-TMBS (Osmol/kg) |
| 5% | 0.152 | 0.132 | 0.143 | 0.123 |
| 10% | 0.307 | 0.296 | 0.275 | 0.214 |
| 15% | 0.448 | 0.342 | 0.399 | 0.263 |
| 20% | x | 0.387 | 0.543 | 0.328 |
| 25% | 0.621 | 0.678 | 0.698 | 0.447 |
| 30% | 1.321 | 1.216 | 0.962 | 0.987 |
| 40% | 2.606 | 1.819 | 2.077 | 1.521 |
| 50% | 3.626 | 3.534 | 2.775 | 2.533 |

Example 3

Verification of Water Flux of Blended-Type Extracted Materials

The thin film (TW30-1812-100HR) produced by DOW FILMTEC was used. The effective area of the thin film was 64 cm$^2$. A RO pump was used to deliver the solution in the water-feeding end and the draw-solution end. The sweep rate was 25 cm/s. The variations of weight and conductivity of the water-feeding end and the draw-solution end were recorded.

In this example, the verification of forward-osmotic water flux was performed on the extracted materials of P2-TOS and the blended-type extracted materials of P2-TOS and P2-TMBS (the blending ratio was 1:2). The experimental results show that the average water flux of P2-TOS was about 2.0 LMH. The water flux of the disclosed blended-type materials was about 1.3-1.7 LMH, and the average was about 1.4 LMH, which shows that it was close to the flux value of P2-TOS.

Example 4

Analysis of Residual Concentration of Extracted Materials in Water-Rich Layer after Phase Separation After the draw solution was heated to form a phase separation, most of the extracted materials remain in the ionic-rich liquid layer, and only a small part of the extracted materials remain in the water-rich layer. In this example, the residual concentration of the extracted materials of P2-TOS, the extracted materials of P2-TMBS, and the extracted materials of P2-TOS and P2-TMBS with different blending ratios in water-rich layer, at a concentration of 50%, after phase separation was formed at 25° C., 30° C., 35° C., 40° C. and 45° C. was analyzed, and the results are shown in Table 4. Table 4 shows that if P2-TOS and P2-TMBS were blended in a ratio of 1:1 (mole), at 35° C. ($\Delta T$=7° C.), the residual concentration of the extracted materials in the water-rich layer was reduced to 9.3%. If P2-TOS and P2-TMBS were blended in a ratio of 1:2 (mole), at 30° C. ($\Delta T$=5° C.), the residual concentration of the extracted materials in the water-rich layer was further reduced to 8.6%.

TABLE 4

| | blending of P2-TOS and P2-TMBS | | | |
|---|---|---|---|---|
| phase separation concentration | 50% P2-TOS | 1:1 (mole) blending 50% | 1:2 (mole) blending 50% | 50% P2-TMBS |
| concentration 50%-Tc (° C.) | 38 | 28 | 25 | 22 |
| 25° C. residual concentration (%) | * | x | x | 5.3 |
| 30° C. residual concentration (%) | * | 11.1 | 8.6 | 3.8 |
| 35° C. residual concentration (%) | * | 9.3 | 7.4 | 2.4 |
| 40° C. residual concentration (%) | 16.1 | 7.7 | 6.2 | 1.5 |
| 45° C. residual concentration (%) | 10.2 | 6.2 | 5.1 | x | residual calculation: NMR internal concentration analysis
* no phase separation
x: no experimental analysis From the above characteristic analysis, the osmotic pressure and water flux of the extracted materials of P2-TOS are high. Although the osmotic pressure of the disclosed blended-type extracted materials was about 0.76 times that of P2-TOS, and the water flux thereof was about 0.7 times that of P2-TOS, in terms of the residual amount of the extracted materials in the water-rich layer, when the concentration was 50% and the temperature was 40° C., the residual amounts of the two extracted materials were 16.1% and 6.2%, respectively. In terms of subsequent nano thin-film separation operations, compared to the residual amount of 6.2% of the extracted materials, the operating pressure for separating and extracting water from the water layer with a residual concentration of 16.1% needed to be increased by at least about 10 kg/cm$^2$.

In terms of overall energy consumption, although the water flux in the front-end of the disclosed blended-type extracted materials performed poorly, they had more advantages in the phase-separation temperature of the draw solution and the energy consumption of the water-production procedure using the nano thin film in the back-end. As a trade-off, the blended-type extracted materials of P2-TOS and P2-TMBS can reduce the overall operating energy consumption and lower the cost of forward-osmosis extraction applications.

Example 5

Verification of Characteristics of TOS-P2-TMBS and Comparison with Blended-Type Extracted Materials Table 5 shows a comparison of the phase-transition temperatures of the extracted materials of TOS-P2-TMBS (synthetic-type) and the extracted materials of P2-TOS and P2-TMBS (blended with 1:1) at different concentrations. The results show that the phase-transition temperatures of the two were similar.

Table 6 shows the analysis of the residual concentration of the extracted materials of TOS-P2-TMBS (synthetic-type) and the extracted materials of P2-TOS and P2-TMBS (blended with 1:1) in water-rich layer, at a concentration of 50%, after phase separation was formed at 30° C., 35° C., 40° C. and 45° C. The results show that the residual concentrations of the two were quite close, which means that the extracted materials formed by a simple blending method had advantages and competition in adjusting the phase-transition temperature and effectively reducing the residual amount of the extracted materials in the water-rich layer.

TABLE 5

| concentration % | TOS-P2-TMBS | P2-TOS:P2-TMBS 1:1 (blending) |
|---|---|---|
| 5 | 35 | 40 |
| 10 | 28 | 28 |
| 20 | 26 | 26 |
| 30 | 27 | x |
| 50 | 28 | 28 |
| 60 | 30 | 31 |
| 65 | 33 | x |
| 70 | 41 | no phase separation |
| 80 | no phase separation | no phase separation |

TABLE 6

| NMR analysis | P2-TOS:P2TMBS 1:1 (blending) 50%; T$_C$: 28° C. | TOS-P2-TMBS 50%; T$_C$: 28° C. |
|---|---|---|
| 30° C. residual concentration (%) | 11.1 | 12.7 |
| 35° C. residual concentration (%) | 9.3 | 8.3 |

TABLE 6-continued

| NMR analysis | P2-TOS:P2TMBS 1:1 (blending) 50%; $T_C$: 28° C. | TOS-P2-TMBS 50%; $T_C$: 28° C. |
|---|---|---|
| 40° C. residual concentration (%) | 7.7 | 6.9 |
| 45° C. residual concentration (%) | 6.2 | 6.5 |

Example 6

Verification of Characteristics of Blended-Type Extracted Materials

A test of phase-transition temperature was performed on the extracted materials of P1-Mal, the extracted materials of P2-TOS, the extracted materials of P2-TMBS, and the extracted materials of P2-TOS, P2-TMBS and P1-Mal with different blending ratios. The results of the test of phase-transition temperature are shown in Table 7. Table 7 shows a comparison of the phase-transition temperature of the extracted materials of P1-Mal, the extracted materials of P2-TOS, the extracted materials of P2-TMBS, and the extracted materials of P2-TOS, P2-TMBS and P1-Mal with different blending ratios at different concentrations. The material of P2-TOS had more hydrophilicity than that of P1-Mal and P2-TMBS, and the phase separation of P2-TOS occurred at higher temperatures. For the extracted materials of P2-TOS, P2-TMBS and P1-Mal with different blending ratios, the phase-transition temperature thereof was between those of P2-TOS and P2-TMBS, and as the blending ratio of P2-TOS decreased, the phase-transition temperature also dropped slightly. From the results in Table 7, it can be verified that the blended-type extracted materials of the present disclosure produce phase separation at low temperature.

TABLE 7

| | phase-transition temperature (° C.) | | | | |
|---|---|---|---|---|---|
| concentration | | P2-TOS:P2-TMBS:P1-Mal blending molar ratios | | | |
| % | P1-Mal | 0.35:0.36:0.29 | 0.45:0.30:0.25 | P2-TOS | P2-TMBS |
| 5% | no phase separation | 39 | 42 | 66 | 25 |
| 10% | 33 | 27 | 28 | 44 | 21 |
| 20% | 25.5 | 24 | 25 | 36 | 20 |
| 30% | 22 | x | x | 35 | 20 |
| 50% | 23 | 26 | 27 | 38 | x |
| 60% | 24 | 28 | 30 | 52 | 23 |
| 70% | 38 | no phase separation | no phase separation | no phase separation | 32 |
| 80% | no phase separation | no phase separation | no phase separation | no phase separation | no phase separation |

Note:
x no measurement

Example 7

Energy Consumption and Cost Estimation of Blended-Type Extracted Materials

In this example, the residual concentration of the extracted materials of P2-TOS and the extracted materials of P2-TOS and P2-TMBS with different blending ratios in water-rich layer, at a concentration of 50%, after phase separation was formed at 40° C. was analyzed, and the energy consumption and cost of electricity required for the separation procedure using the nano thin film in the back-end was estimated. The results are shown in Table 8. Table 8 indicates that if P2-TOS and P2-TMBS were blended in a ratio of 1:1 (mole), the residual concentration of the extracted materials in the water-rich layer was reduced to 7.7%. If P2-TOS and P2-TMBS were blended in a ratio of 1:2 (mole), the residual concentration of the extracted materials in the water-rich layer was further reduced to 6.2%. Also, the energy consumption and cost of electricity required for the separation procedure using the nano thin film in the back-end was significantly reduced.

TABLE 8

| | | blending of P2-TOS and P2-TMBS | |
|---|---|---|---|
| phase-separation concentration 1 | 50% P2-TOS | 1:1 (mole) blending 50% | 1:2 (mole) blending 50% |
| 40° C. residual concentration (%) | 16.1 | 7.7 | 6.2 |
| energy consumption required for separation (kWh/m³) | 2.0 | 1.0 | 0.8 |
| cost of electricity required for separation (NT/m³) | 5.2 | 2.6 | 2.1 |

While the invention has been described by way of example and in terms of the preferred embodiments, it should be understood that the invention is not limited to the disclosed embodiments. On the contrary, it is intended to cover various modifications and similar arrangements (as would be apparent to those skilled in the art). Therefore, the scope of the appended claims should be accorded the broadest interpretation so as to encompass all such modifications and similar arrangements.

What is claimed is:

1. An ionic composition for forward osmosis, comprising:
   a first ionic compound;
   a second ionic compound; and
   a third ionic compound, wherein the first ionic compound, the second ionic compound and the third ionic compound are represented by formula (I):

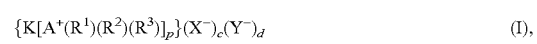

wherein $R^1$, $R^2$ and $R^3$ independently comprise straight or branched C1-12 alkyl, A comprises phosphorus or nitrogen, K comprises C1-15 alkyl and both ends thereof are connected to $[A^+(R^1)(R^2)(R^3)]$, p=2, c and d are integers, c+d=2, and $X^-$ and $Y^-$ comprise $CH_3SO_3^-$, $I^-$, $CF_3COO^-$, $SCN^-$, $BF_4^-$, $CF_3SO_3^-$, $PF_6^-$, $FeCl_4^-$,

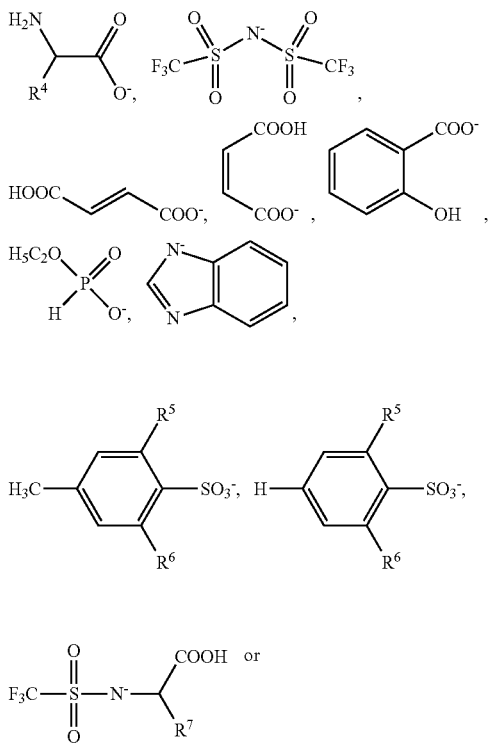

wherein $R^4$ is —$CH_2COOH$ or —$(CH_2)_4$—$NH_2$, $R^5$ and $R^6$ are H or $CH_3$, $R^7$ is —$CH(CH_3)_2$, —$(CH_2)_2$—$CH(CH_3)_2$, —$CH(CH_3)$—$CH_2$—$CH_3$ or —$CH_2$—$C_6H_5$, and $R^8$ is $CH_3$ or H, wherein the group $X^-$ is the same as the group $Y^-$ in the first ionic compound, the group $X^-$ is the same as the group $Y^-$ in the second ionic compound, and the group $X^-$ in the first ionic compound is different from the group $X^-$ in the second ionic compound, and the group $X^-$ differs from the group $Y^-$ in the third ionic compound, the group $X^-$ in the third ionic compound is the same as the group $X^-$ in the first ionic compound or the group $X^-$ in the second ionic compound, and the group $Y^-$ in the third ionic compound is the same as the group $Y^-$ in the first ionic compound or the group $Y^-$ in the second ionic compound.

2. The ionic composition for forward osmosis as claimed in claim 1, wherein the first ionic compound and the second ionic compound comprise

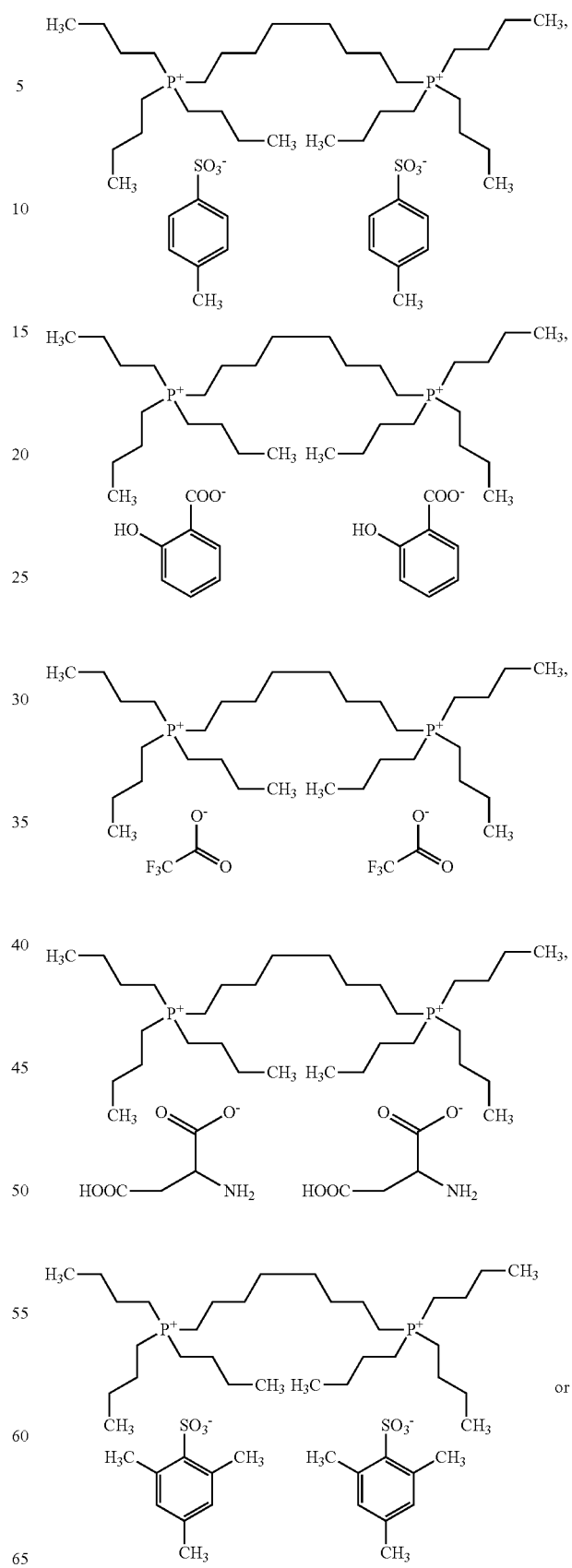

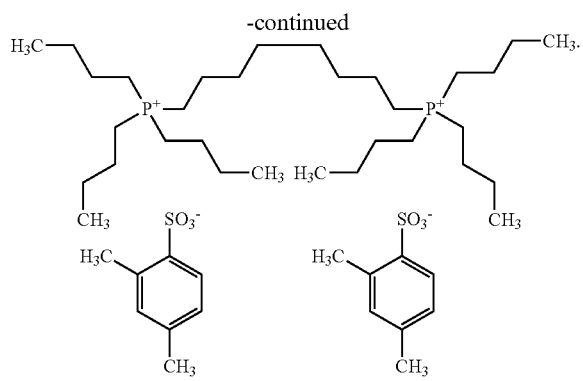

3. The ionic composition for forward osmosis as claimed in claim 1, wherein the third ionic compound comprises

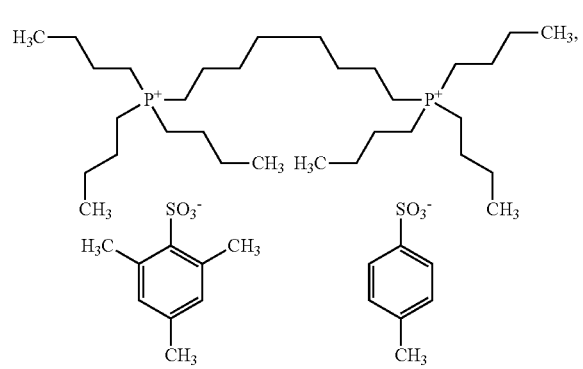

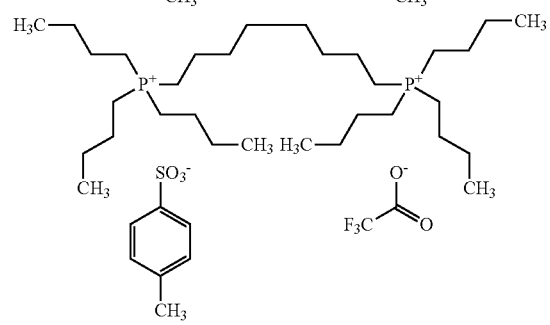

or

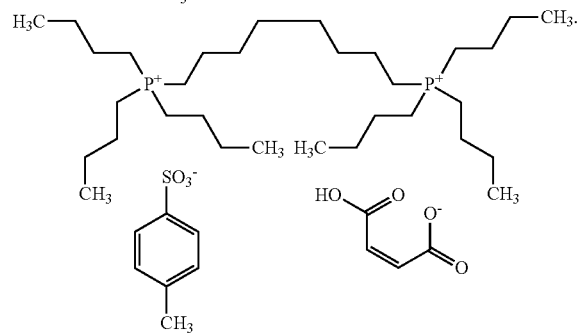

4. The ionic composition for forward osmosis as claimed in claim 1, further comprising a fourth ionic compound which is represented by formula (II):

$$[A^+(R^1)(R^2)(R^3)(R^4)]_n(X^-)_a \quad (II),$$

wherein $R^1$, $R^2$, $R^3$ and $R^4$ independently comprise straight or branched C1-12 alkyl, A comprises phosphorus or nitrogen, n=1, a=1, and $X^-$ comprises $CH_3SO_3^-$, $I^-$, $CF_3COO^-$, $SCN^-$, $BF_4^-$, $CF_3SO_3^-$, $PF_6^-$, $FeCl_4^-$,

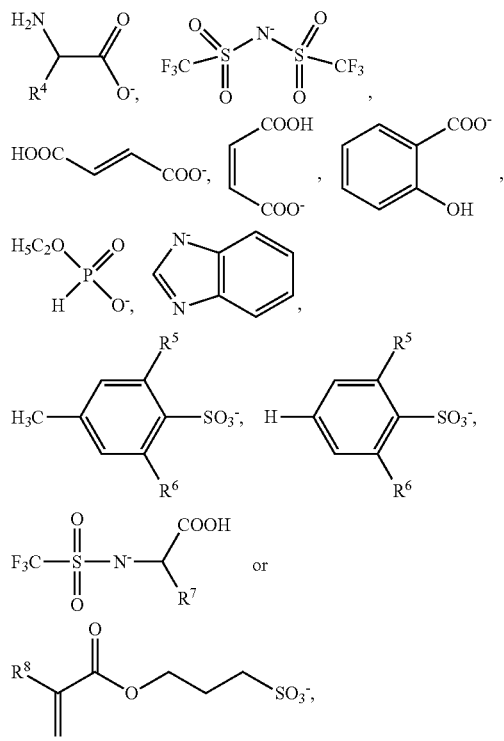

wherein $R^4$ is $—CH_2COOH$ or $—(CH_2)_4—NH_2$, $R^5$ and $R^6$ are H or $CH_3$, $R^7$ is $—CH(CH_3)_2$, $—(CH_2)_2—CH(CH_3)_2$, $—CH(CH_3)—CH_2—CH_3$ or $—CH_2—C_6H_5$, and $R^8$ is $CH_3$ or H.

5. The ionic composition for forward osmosis as claimed in claim 4, wherein the fourth ionic compound comprises

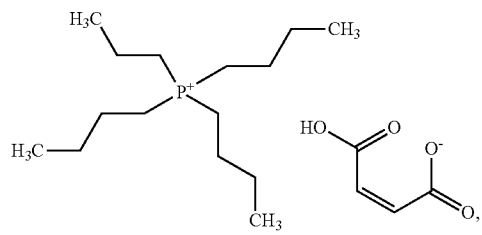

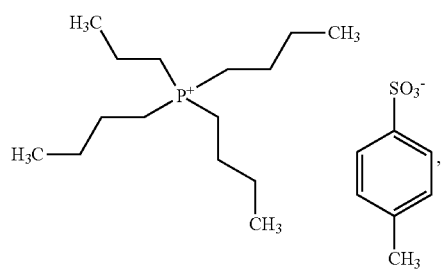

-continued

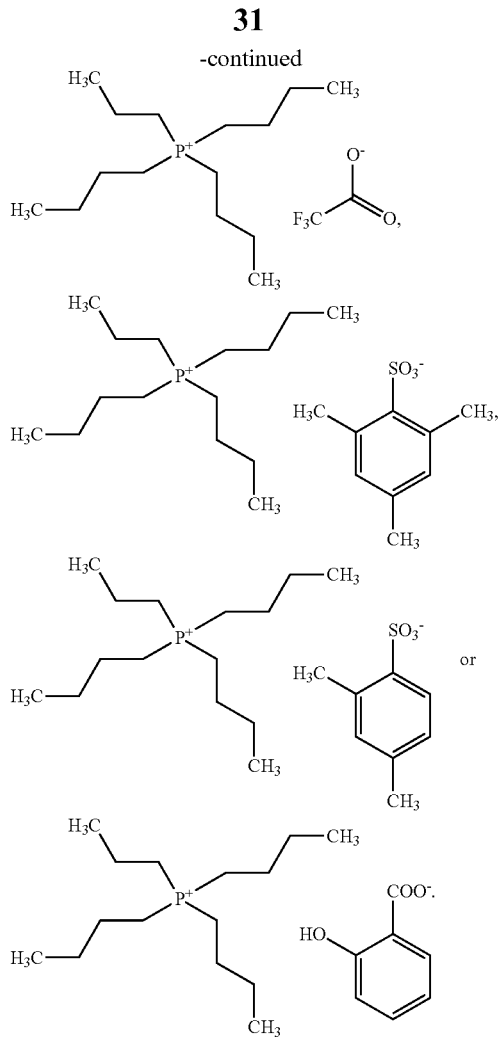

6. The ionic composition for forward osmosis as claimed in claim 1, further comprising a fifth ionic compound which is represented by formula (III):

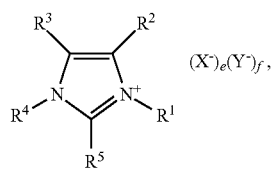
(III)

wherein $R^1$, $R^2$, $R^3$, $R^4$ and $R^5$ independently comprise straight or branched C1-12 alkyl, $X^-$ and $Y^-$ independently comprise organic or inorganic anions, e and f are zero or an integer and e+f=1.

7. The ionic composition for forward osmosis as claimed in claim 6, wherein, in formula (III), $X^-$ and $Y^-$ comprise $CH_3SO_3^-$, $I^-$, $CF_3COO^-$, $SCN^-$, $BF_4^-$, $CF_3SO_3^-$, $PF_6^-$, $FeCl_4^-$,

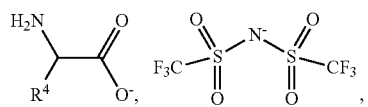

-continued

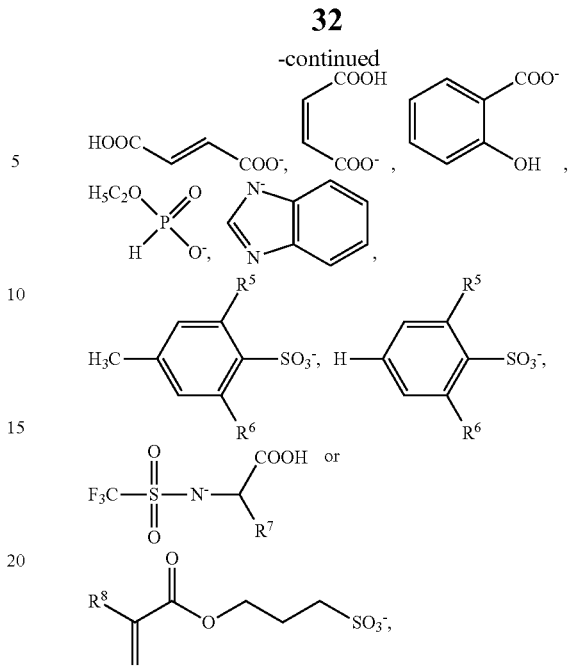

wherein $R^4$ is —$CH_2COOH$ or —$(CH_2)_4$—$NH_2$, $R^5$ and $R^6$ are H or $CH_3$, $R^7$ is —$CH(CH_3)_2$, —$(CH_2)_2$—$CH(CH_3)_2$, —$CH(CH_3)$—$CH_2$—$CH_3$ or —$CH_2$—$C_6H_5$, and $R^8$ is $CH_3$ or H.

8. The ionic composition for forward osmosis as claimed in claim 1, wherein the extracted material has a phase-transition temperature which is in a range from 20° C. to 50° C.

9. A forward-osmosis water desalination system, comprising:
a feeding unit comprising a feeding end and a draw-solution end separated from the feeding end by a semi-permeable membrane, wherein the feeding end comprises raw water, and the draw-solution end comprises the extracted material as claimed in claim 1;
a phase-separation unit connected to the feeding unit, the phase-separation unit comprising an aqueous layer and an ionic liquid layer, wherein the extracted material has a concentration in the ionic liquid layer which is greater than that in the aqueous layer; and
a recovery unit connected to the phase-separation unit and filtering the aqueous layer to recover pure water.

10. The forward-osmosis water desalination system as claimed in claim 9, wherein the concentration of the extracted material is less than 10% in the aqueous layer in the phase-separation unit.

11. The forward-osmosis water desalination system as claimed in claim 9, wherein the concentration of the extracted material is in a range from 10% to 70% in the ionic liquid layer in the phase-separation unit.

12. The forward-osmosis water desalination system as claimed in claim 9, wherein the phase-separation unit has an operating temperature which is in a range from 20° C. to 50° C.

13. The forward-osmosis water desalination system as claimed in claim 9, wherein the recovery unit further comprises a thin film to filter the aqueous layer introduced from the phase-separation unit.

14. A method for preparing an extracted material, comprising:

providing a first ionic compound and a second ionic compound, wherein the first ionic compound and the second ionic compound are represented by formula (I):

  (I), wherein $R^1$, $R^2$ and $R^3$ independently comprise straight or branched C1-12 alkyl, A comprises phosphorus or nitrogen, K comprises C1-15 alkyl and both ends thereof are connected to $[A^+(R^1)(R^2)(R^3)]$, p=2, c and d are integers, c+d=2, and $X^-$ and $Y^-$ comprise $CH_3SO_3^-$, $I^-$, $CF_3COO^-$, $SCN^-$, $BF_4^-$, $CF_3SO_3^-$, $PF_6^-$, $FeCl_4^-$,

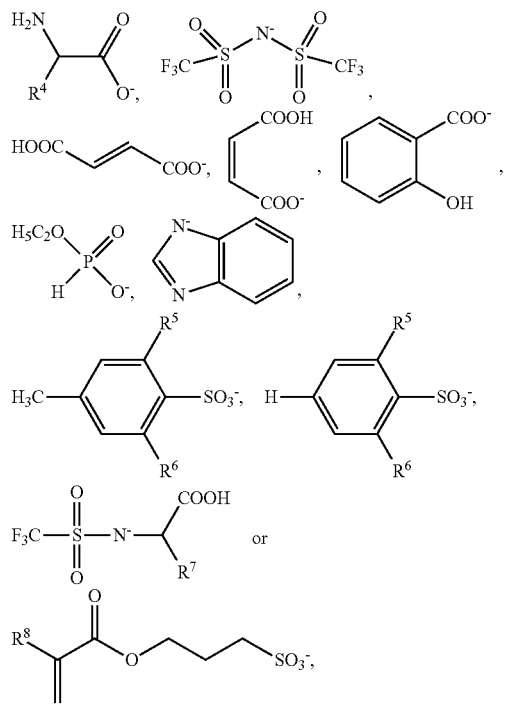

wherein $R^4$ is $-CH_2COOH$ or $-(CH_2)_4-NH_2$, $R^5$ and $R^6$ are H or $CH_3$, $R^7$ is $-CH(CH_3)_2$, $-(CH_2)_2-CH(CH_3)_2$, $-CH(CH_3)-CH_2-CH_3$ or $-CH_2-C_6H_5$, and $R^8$ is $CH_3$ or H, wherein the group $X^-$ is the same as the group $Y^-$ in the first ionic compound, the group $X^-$ is the same as the group $Y^-$ in the second ionic compound, and the group $X^-$ in the first ionic compound is different from the group $X^-$ in the second ionic compound; and blending the first ionic compound and the second ionic compound to prepare an extraction material, wherein the first ionic compound and the second ionic compound have a molar ratio which is in a range from 0.05:0.95 to 0.95:0.05.

15. The method for preparing an extracted material as claimed in claim 14, wherein the molar ratio of the first ionic compound to the second ionic compound is in a range from 0.15:0.85 to 0.85:0.15.

16. The method for preparing an extracted material as claimed in claim 14, further comprising blending a fourth ionic compound which is represented by formula (II):

  (II), wherein $R^1$, $R^2$, $R^3$ and $R^4$ independently comprise straight or branched C1-12 alkyl, A comprises phosphorus or nitrogen, n=1, a=1, and $X^-$ comprises $CH_3SO_3^-$, $I^-$, $CF_3COO^-$, $SCN^-$, $BF_4^-$, $CF_3SO_3^-$, $PF_6^-$, $FeCl_4^-$,

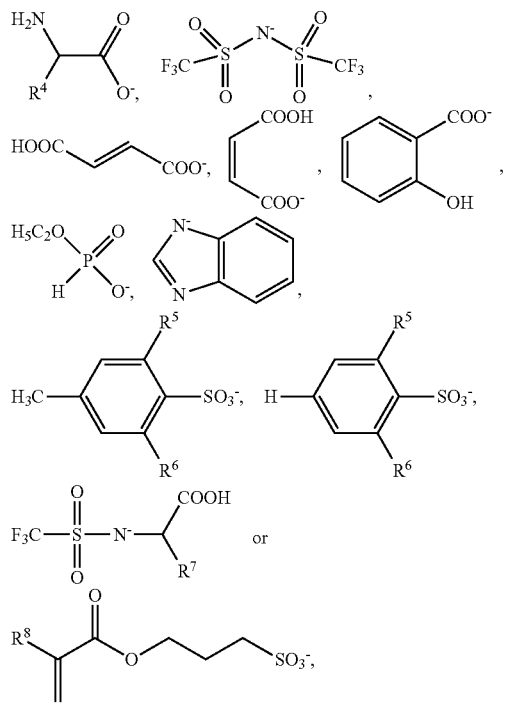

wherein $R^4$ is $-CH_2COOH$ or $-(CH_2)_4-NH_2$, $R^5$ and $R^6$ are H or $CH_3$, $R^7$ is $-CH(CH_3)_2$, $-(CH_2)_2-CH(CH_3)_2$, $-CH(CH_3)-CH_2-CH_3$ or $-CH_2-C_6H_5$, and $R^8$ is $CH_3$ or H.

17. The method for preparing an extracted material as claimed in claim 14, further comprising blending a fifth ionic compound which is represented by formula (III):

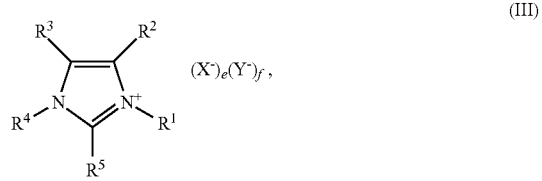

wherein $R^1$, $R^2$, $R^3$, $R^4$ and $R^5$ independently comprise straight or branched C1-12 alkyl, $X^-$ and $Y^-$ independently comprise organic or inorganic anions, and e and f are zero or an integer e+f=1.

18. The method for preparing an extracted material as claimed in claim 17, wherein, in formula (III), $X^-$ and $Y^-$ comprise $CH_3SO_3^-$, $I^-$, $CF_3COO^-$, $SCN^-$, $BF_4^-$, $CF_3SO_3^-$, $PF_6^-$, $FeCl_4^-$,

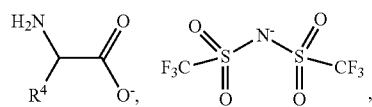

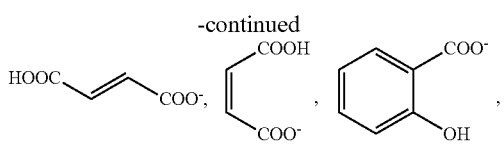
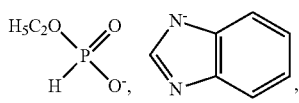
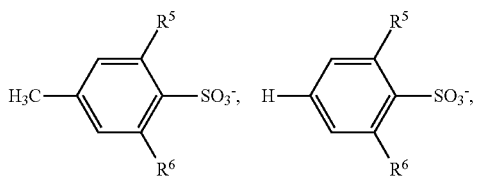
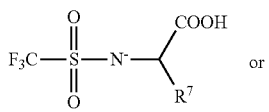

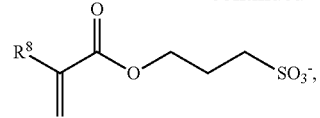

wherein $R^4$ is —$CH_2COOH$ or —$(CH_2)_4$—$NH_2$, $R^5$ and $R^6$ are H or $CH_3$, $R^7$ is —$CH(CH_3)_2$, —$(CH_2)_2$—$CH(CH_3)_2$, —$CH(CH_3)$—$CH_2$—$CH_3$ or —$CH_2$—$C_6H_5$, and $R^8$ is $CH_3$ or H.

19. The method for preparing an extracted material as claimed in claim 16, wherein the first ionic compound, the second ionic compound and the fourth ionic compound have a molar ratio of 0.05-0.90:0.05-0.90:0.05-0.90.

20. The method for preparing an extracted material as claimed in claim 16, wherein the first ionic compound, the second ionic compound and the fourth ionic compound have a molar ratio of 0.10-0.80:0.10-0.80:0.10-0.80.

21. The method for preparing an extracted material as claimed in claim 17, wherein the first ionic compound, the second ionic compound and the fifth ionic compound have a molar ratio of 0.05-0.90:0.05-0.90:0.05-0.90.

22. The method for preparing an extracted material as claimed in claim 17, wherein the first ionic compound, the second ionic compound and the fifth ionic compound have a molar ratio of 0.10-0.80:0.10-0.80:0.10-0.80.

* * * * *